(12) United States Patent
Logan et al.

(10) Patent No.: US 12,673,183 B2
(45) Date of Patent: Jul. 7, 2026

(54) HIGH FLEXIBILITY, KINK RESISTANT CATHETER SHAFT

(71) Applicant: Perfuze Limited, Galway (IE)

(72) Inventors: John Logan, Plymouth, MN (US); Scott Arp, Miami, FL (US); Andrew H. Cragg, Edina, MN (US)

(73) Assignee: Perfuze Limited, Galway (IE)

( * ) Notice: Subject to any disclaimer, the term of this patent is extended or adjusted under 35 U.S.C. 154(b) by 0 days.

(21) Appl. No.: 17/886,199

(22) Filed: Aug. 11, 2022

(65) Prior Publication Data

US 2022/0379078 A1 Dec. 1, 2022

Related U.S. Application Data

(63) Continuation of application No. 15/647,763, filed on Jul. 12, 2017, now Pat. No. 11,446,469.

(Continued)

(51) Int. Cl.
A61M 25/00 (2006.01)
A61F 2/95 (2013.01)
(Continued)

(52) U.S. Cl.
CPC ........... A61M 25/0045 (2013.01); A61F 2/95 (2013.01); A61M 25/001 (2013.01);
(Continued)

(58) Field of Classification Search
CPC . A61B 1/005; A61M 25/0053; A61M 25/005; A61M 25/0054; A61M 25/0013;
(Continued)

(56) References Cited

U.S. PATENT DOCUMENTS

| | | | | |
|---|---|---|---|---|
| 4,784,639 A | | 11/1988 | Patel | |
| 5,358,493 A | * | 10/1994 | Schweich, Jr. ... | A61M 25/0054 |
| | | | | 604/525 |

(Continued)

FOREIGN PATENT DOCUMENTS

| | | |
|---|---|---|
| EP | 0421650 A1 | 4/1991 |
| EP | 0 861 674 A1 | 9/1998 |

(Continued)

OTHER PUBLICATIONS

Extended European Search Report in EP 22162759.9-1122, dated Jun. 24, 2022 (9 pages).
T.V. How et al. "Expanded Polytetrafluoroethylene" ScienceDirect, Handbook of Polymer Applications in Medicine and Medical Device, 2014, (8 pages).
Translation of Notice of Opposition filed in European Patent No. 3484568. (30 pages).

*Primary Examiner* — Kevin C Sirmons
*Assistant Examiner* — Alexandra Lalonde
(74) *Attorney, Agent, or Firm* — Bookoff McAndrews, PLLC

(57) ABSTRACT

An enhanced flexibility catheter shaft having an elongate flexible body with a proximal end, a distal end, and at least one lumen extending therethrough. A distal, flexible section on the body has a ribbed or corrugated tubular membrane having at least a first reinforcement structure, such as a first helical support, on a radially exterior or interior surface of the membrane and optionally a second reinforcement structure, such as a second helical support, on the other of the radially interior or exterior surface of the membrane.

20 Claims, 11 Drawing Sheets

Related U.S. Application Data

(60) Provisional application No. 62/361,984, filed on Jul. 13, 2016.

(51) Int. Cl.
| | |
|---|---|
| *A61M 25/01* | (2006.01) |
| *A61M 25/09* | (2006.01) |
| *A61M 25/10* | (2013.01) |

(52) U.S. Cl.
CPC ...... *A61M 25/0012* (2013.01); *A61M 25/005* (2013.01); *A61M 25/0054* (2013.01); *A61M 25/0108* (2013.01); *A61M 25/09* (2013.01); *A61M 25/0052* (2013.01); *A61M 25/0053* (2013.01); *A61M 2025/0059* (2013.01); *A61M 25/0068* (2013.01); *A61M 25/10* (2013.01)

(58) Field of Classification Search
CPC .......... A61M 25/0012; A61M 25/0051; A61M 25/0045; A61M 25/0052; A61M 25/0068; A61M 2025/006; A61M 2025/1088; A61M 2025/0062; A61M 2025/0081; A61M 25/0021; A61M 25/008; A61M 25/001; A61M 25/0108; A61M 25/09; A61M 25/10; A61M 25/00; A61M 25/0138; A61M 25/0141; A61M 25/0144; A61M 2025/0059; A61M 2025/0046; A61F 2/95

See application file for complete search history.

(56) References Cited

U.S. PATENT DOCUMENTS

| | | | | |
|---|---|---|---|---|
| 5,405,338 | A * | 4/1995 | Kranys | A61M 25/005 |
| | | | | 604/524 |
| 5,460,170 | A | 10/1995 | Hammerslag | |
| 5,507,995 | A | 4/1996 | Schweich et al. | |
| 5,662,622 | A | 9/1997 | Gore | |
| 5,700,253 | A | 12/1997 | Parker | |
| 5,792,116 | A * | 8/1998 | Berg | A61M 25/0023 |
| | | | | 600/585 |
| 5,800,522 | A | 9/1998 | Campbell | |
| 5,865,723 | A | 2/1999 | Love | |
| 5,873,866 | A | 2/1999 | Kondo et al. | |
| 5,876,386 | A | 3/1999 | Samson | |
| 5,879,342 | A | 3/1999 | Kelley | |
| 5,938,587 | A | 8/1999 | Taylor et al. | |
| 5,951,539 | A | 9/1999 | Nita et al. | |
| 5,980,505 | A | 11/1999 | Wilson | |
| 6,004,310 | A | 12/1999 | Bardsley et al. | |
| 6,171,297 | B1 | 1/2001 | Pedersen et al. | |
| 6,217,566 | B1 | 4/2001 | Ju et al. | |
| 6,358,238 | B1 | 3/2002 | Sherry | |
| 6,464,632 | B1 * | 10/2002 | Taylor | A61B 1/005 |
| | | | | 138/174 |
| 6,464,684 | B1 | 10/2002 | Galdonik | |
| 6,482,171 | B1 | 11/2002 | Corvi et al. | |
| 6,500,285 | B2 * | 12/2002 | Pepin | A61M 25/0014 |
| | | | | 156/158 |
| 6,508,806 | B1 | 1/2003 | Hoste | |
| 6,591,472 | B1 * | 7/2003 | Noone | A61M 25/0045 |
| | | | | 264/171.18 |
| 6,616,651 | B1 | 9/2003 | Stevens | |
| 6,652,508 | B2 | 11/2003 | Griffin et al. | |
| 6,689,120 | B1 | 2/2004 | Gerdts | |
| 6,709,429 | B1 | 3/2004 | Schaefer et al. | |
| 6,824,553 | B1 | 11/2004 | Samson et al. | |
| 6,858,024 | B1 | 2/2005 | Berg et al. | |
| 7,001,369 | B2 | 2/2006 | Griffin et al. | |
| 7,273,485 | B2 | 9/2007 | Simpson et al. | |
| 7,674,239 | B2 | 3/2010 | Sisken et al. | |
| 7,704,245 | B2 | 4/2010 | Dittman et al. | |
| 7,815,599 | B2 | 10/2010 | Griffin et al. | |
| 7,815,608 | B2 | 10/2010 | Schafersman et al. | |
| 7,815,762 | B2 | 10/2010 | Lentz et al. | |
| 7,914,466 | B2 | 3/2011 | Davis et al. | |
| 8,021,352 | B2 | 9/2011 | Slazas et al. | |
| 8,070,898 | B2 | 12/2011 | Eversull et al. | |
| 8,092,374 | B2 | 1/2012 | Smith et al. | |
| 8,114,144 | B2 | 2/2012 | Chow et al. | |
| 8,292,802 | B2 | 10/2012 | Smith et al. | |
| 8,343,136 | B2 | 1/2013 | Howat et al. | |
| 8,366,699 | B2 | 2/2013 | Jimenez et al. | |
| 8,454,578 | B2 | 6/2013 | Leeflang et al. | |
| 8,486,048 | B2 | 7/2013 | Kubo et al. | |
| 8,523,899 | B2 | 9/2013 | Suzuki | |
| 8,591,495 | B2 | 11/2013 | Fischel et al. | |
| 8,608,690 | B2 | 12/2013 | Pal | |
| 8,636,716 | B2 | 1/2014 | Griffin et al. | |
| 8,652,098 | B2 | 2/2014 | Haslinger | |
| 8,663,196 | B2 | 3/2014 | Kassab et al. | |
| 8,663,197 | B2 | 3/2014 | Ogura et al. | |
| 8,702,680 | B2 | 4/2014 | Jimenez et al. | |
| 8,708,997 | B2 | 4/2014 | Parker | |
| 8,715,441 | B2 | 5/2014 | Brustad et al. | |
| 8,734,699 | B2 | 5/2014 | Heideman et al. | |
| 8,870,790 | B2 | 10/2014 | Davis et al. | |
| 8,926,560 | B2 | 1/2015 | Dinh et al. | |
| 9,022,977 | B2 | 5/2015 | Rosenman et al. | |
| 9,119,740 | B2 | 9/2015 | Cannon et al. | |
| 9,157,558 | B2 * | 10/2015 | Hudson | F16L 11/088 |
| 9,339,629 | B2 | 5/2016 | Watanabe et al. | |
| 9,352,123 | B2 | 5/2016 | Zhou et al. | |
| 9,365,018 | B2 | 6/2016 | Drewes, Jr. et al. | |
| 9,370,639 | B2 * | 6/2016 | Plassman | A61M 25/0054 |
| 9,393,380 | B2 | 7/2016 | Merk et al. | |
| 9,399,114 | B2 | 7/2016 | Parker | |
| 9,597,481 | B2 | 3/2017 | Ishikawa | |
| 10,188,413 | B1 | 1/2019 | Morriss | |
| 2001/0027310 | A1 * | 10/2001 | Parisi | A61M 25/005 |
| | | | | 604/524 |
| 2001/0034514 | A1 | 10/2001 | Parker | |
| 2002/0058910 | A1 | 5/2002 | Hermann et al. | |
| 2002/0132076 | A1 | 9/2002 | Stevens | |
| 2002/0156460 | A1 | 10/2002 | Ye et al. | |
| 2003/0028153 | A1 | 2/2003 | Brennan | |
| 2003/0135198 | A1 | 7/2003 | Berhow et al. | |
| 2004/0220549 | A1 | 11/2004 | Dittman et al. | |
| 2004/0243102 | A1 * | 12/2004 | Berg | A61M 25/0054 |
| | | | | 604/525 |
| 2005/0165366 | A1 | 7/2005 | Brustad et al. | |
| 2006/0030835 | A1 | 2/2006 | Sherman et al. | |
| 2006/0200110 | A1 | 9/2006 | Lentz et al. | |
| 2006/0229589 | A1 | 10/2006 | Itou et al. | |
| 2006/0259118 | A1 | 11/2006 | Pal et al. | |
| 2006/0264904 | A1 | 11/2006 | Kerby | |
| 2007/0083132 | A1 * | 4/2007 | Sharrow | A61M 25/0012 |
| | | | | 600/431 |
| 2007/0088323 | A1 | 4/2007 | Campbell | |
| 2007/0225680 | A1 | 9/2007 | Biggin et al. | |
| 2007/0255105 | A1 | 11/2007 | Ochi | |
| 2008/0108974 | A1 | 5/2008 | Yee Roth | |
| 2008/0119825 | A1 | 5/2008 | Imai et al. | |
| 2009/0030400 | A1 | 1/2009 | Bose | |
| 2009/0149834 | A1 | 6/2009 | Moss | |
| 2009/0236770 | A1 | 9/2009 | Fogarty | |
| 2009/0240236 | A1 * | 9/2009 | Fogarty | B29C 70/70 |
| | | | | 138/140 |
| 2010/0049167 | A1 | 2/2010 | Myers | |
| 2010/0145313 | A1 | 6/2010 | Packard | |
| 2010/0180976 | A1 | 7/2010 | Witz et al. | |
| 2011/0112567 | A1 | 5/2011 | Lenker et al. | |
| 2011/0245775 | A1 | 10/2011 | Tekulve | |
| 2011/0288532 | A1 | 11/2011 | Faherty et al. | |
| 2011/0319754 | A1 | 12/2011 | Solar et al. | |
| 2012/0078187 | A1 | 3/2012 | Delap | |
| 2012/0277729 | A1 | 11/2012 | Melsheimer | |
| 2013/0090632 | A1 | 4/2013 | Tahara et al. | |
| 2013/0095228 | A1 | 4/2013 | Howat et al. | |
| 2014/0046297 | A1 | 2/2014 | Shimada et al. | |
| 2015/0025562 | A1 | 1/2015 | Dinh | |
| 2015/0174364 | A1 | 6/2015 | Kennelly et al. | |

(56)          References Cited

U.S. PATENT DOCUMENTS

| 2015/0217083 | A1 | 8/2015 | Richter et al. |
| 2015/0273184 | A1 | 10/2015 | Scott et al. |
| 2015/0306347 | A1 | 10/2015 | Yagi |
| 2015/0320971 | A1 | 11/2015 | Leeflang |
| 2016/0001040 | A1 | 1/2016 | Yamaguchi et al. |
| 2016/0030704 | A1 | 2/2016 | Nishigishi |
| 2016/0121077 | A1 | 5/2016 | Ingalls et al. |
| 2016/0296731 | A1 | 10/2016 | Merk et al. |
| 2016/0346507 | A1* | 12/2016 | Jackson ............ A61M 25/0012 |
| 2017/0000973 | A1 | 1/2017 | Otake et al. |
| 2017/0000977 | A1 | 1/2017 | Storbeck |
| 2017/0043119 | A1 | 2/2017 | Kubo et al. |

| 2017/0072163 | A1* | 3/2017 | Lim .................. A61M 25/0053 |
| 2018/0015248 | A1 | 1/2018 | Logan et al. |

FOREIGN PATENT DOCUMENTS

| EP | 1270031 A1 | 1/2003 |
| EP | 2572749 A3 | 3/2013 |
| JP | H09-506541 A | 6/1997 |
| JP | H10-263088 A | 10/1998 |
| JP | 2013-162979 A | 8/2013 |
| JP | 2014-508564 A | 4/2014 |
| WO | WO 93/15784 | 8/1993 |
| WO | WO 1994019039 A1 | 9/1994 |
| WO | WO 2015/099935 A1 | 7/2015 |

* cited by examiner

PROXIMAL END

PROXIMAL (MID SECTION)

DISTAL

HIGH FLEXIBILITY, KINK RESISTANT CATHETER SHAFT

INCORPORATION BY REFERENCE TO ANY PRIORITY APPLICATIONS

This application is a continuation of U.S. application Ser. No. 15/647,763, filed on Jul. 12, 2017 and claims the benefit of U.S. Provisional Application No. 62/361,984, filed Jul. 13, 2016, both of which are hereby incorporated by reference in their entirety herein.

Any and all applications for which a foreign or domestic priority claim is identified in the Application Data Sheet as filed with the present application are hereby incorporated by reference under 37 CFR 1.57.

BACKGROUND

Field

The present disclosure relates to a flexible catheter for endovascular procedures.

Description of the Related Art

Nearly all endovascular procedures require the use of flexible catheters, for example, to deliver contrast injection, to deliver implantable devices, perform vascular procedures, or to aspirate. Due to the tortuous nature of the vasculature, it is important for catheters to be flexible enough to travel through vessels without excessive force. However, there is generally a trade-off between the features of catheter diameter, trackability, flexibility, and kink resistance. An increase in catheter diameter tends to increase its stiffness, which lowers its trackability and may dangerously increase vascular sheer forces. An increase in flexibility tends to increase the tendency of the catheter to kink as it is pushed through the vasculature, which limits the catheter to vessels with gentle curves.

SUMMARY

Traditional catheter shafts have a braided/coiled wire reinforcing element encapsulated in a plastic matrix to form a tube. The catheter shaft may or may not have a coaxial liner layer. With these conventional designs, the inherent flexibility of the base wire frame is significantly reduced when encapsulated in the non-distensible plastic matrix. To facilitate trackability, some catheter designs vary the inner/outer diameter of the catheter and/or the durometer of the plastic material. However, when the resulting reinforced tube is flexed, a great deal of energy goes into stretching the plastic matrix on the outside curve and compressing the plastic matrix on the inside curve of the tube. This is less pronounced on small diameter catheters, but more significant as diameter gets larger. Further, varying the durometer creates potential kinking points at the durometer transition points. This conventional construction also provides limited force transmission or pushability due to buckling or ovalization of the distal shaft. It would be desirable to have a catheter that did not show deteriorating trackability and kink resistance as the diameter increased.

The present disclosure is directed toward catheter shaft designs that are more flexible than conventional shafts and that demonstrate a unique set of properties such as relative independence of catheter diameter and stiffness, catheter diameter and trackability, and catheter stiffness and kink resistance. The catheter shafts described below permit the passage of larger diameter catheters through tortuous vascular anatomy and to more distal vascular anatomy, while providing improved resistance to compression or ovalization during bending. This increase in flexibility is coupled with an improved kink resistance for a given catheter diameter.

Some aspects of the disclosure are directed toward an elongate flexible body with a proximal end, a distal end, and at least one lumen extending therethrough. A distal, flexible section on the body has a tubular membrane having at least a first reinforcement structure, such as a first helical support, on a radially interior or exterior surface of the membrane. A second reinforcement structure, such as a second helical support, on the other of the radially interior or exterior surface of the membrane may also be provided.

Controlled hinging (e.g., pleating or corrugating) of the tubular membrane during bending reduces the tendency of the tubular membrane to buckle or kink at a focal bending point. In some embodiments, the tubular membrane is supported by opposing inner and outer coils as described above, which can promote the controlled hinging. In some embodiments, the tubular membrane is supported by only an outer coil or an inner coil that is affixed to the tubular membrane by an ultra-thin layer of a suitable plastic, such as Kynar, that does not restrict the pleating of the tubular membrane.

Some aspects of the disclosure are directed toward a highly flexible, kink resistant catheter with floating tubular support. The catheter can include an elongate tubular body having a proximal end, a distal end and a central lumen. The tubular body can include an inner tubular layer surrounding the lumen. A helical support can be carried concentrically over the inner layer. Adjacent loops spaced axially apart. The pitch of the adjacent loops can be varied to adjust for flexibility and pushability. An outer tubular layer can be carried concentrically over the helical support. The inner layer and the outer layer are bonded together in the space between adjacent loops of the tubular support to form a helical channel and the helical support is floating unbonded within the helical channel, e.g., the tubular support is not molecularly or physically attached to the inner layer or the outer layer. The cross sectional area of the helical channel can be varied from an area just larger than the wire cross sectional area to an area up to 10× larger than the wire cross sectional area in order to facilitate free movement of the wire helix.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION

Figure 1:
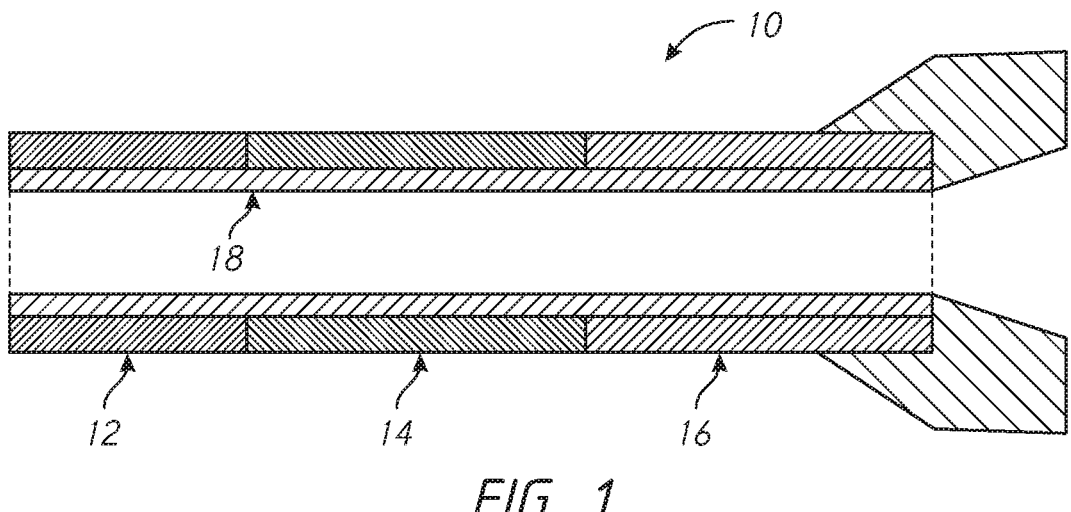
FIG. 1 is a schematic representation of a conventional catheter.

To improve flexibility, conventional catheter designs often vary a durometer of the polymer tubing along the catheter shaft. FIG. 1 schematically illustrates a conventional catheter 10 having a plurality of sections of polymer tubing 12, 14, 16 forming an outer surface of the catheter 10. Each section 12, 14, 16 has a different durometer. Often, the durometer of the polymer tubing transitions every few centimeters. The transition points between the different sections can increase the likelihood of kinking. Further, the softer durometer sections can increase resistance when the outer surface of the catheter contacts a vessel wall.

An inner surface of the catheter 10 can be formed by a liner 18, which can limit flexibility by providing a relatively stiff backbone. A stiffer catheter tends to create increased resistance when the inner surface of the catheter contacts the guide wire and/or the outer surface of the catheter contacts the vessel. The catheter shaft designs described below provide improved flexibility, trackability, and kink resistance, even for catheters having larger diameters.

Fibrous Encapsulated Reinforcement Structure

Figure 2:
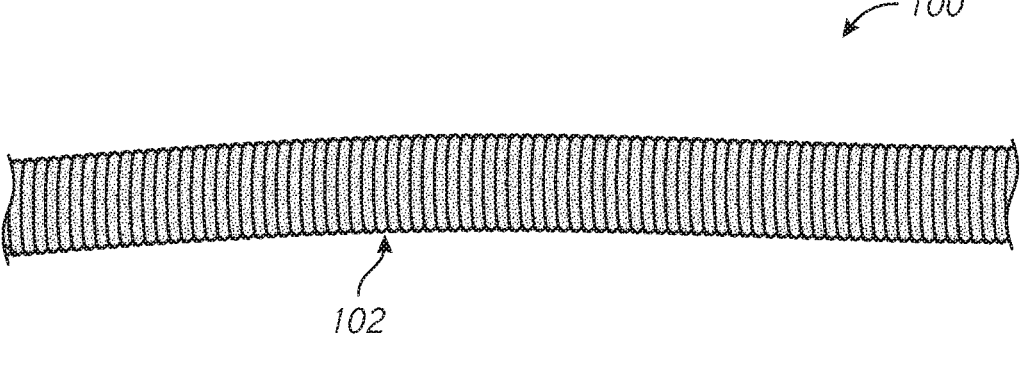
FIG. 2 shows a distal portion of a catheter having a single reinforcement structure.
Figures 3, 4:
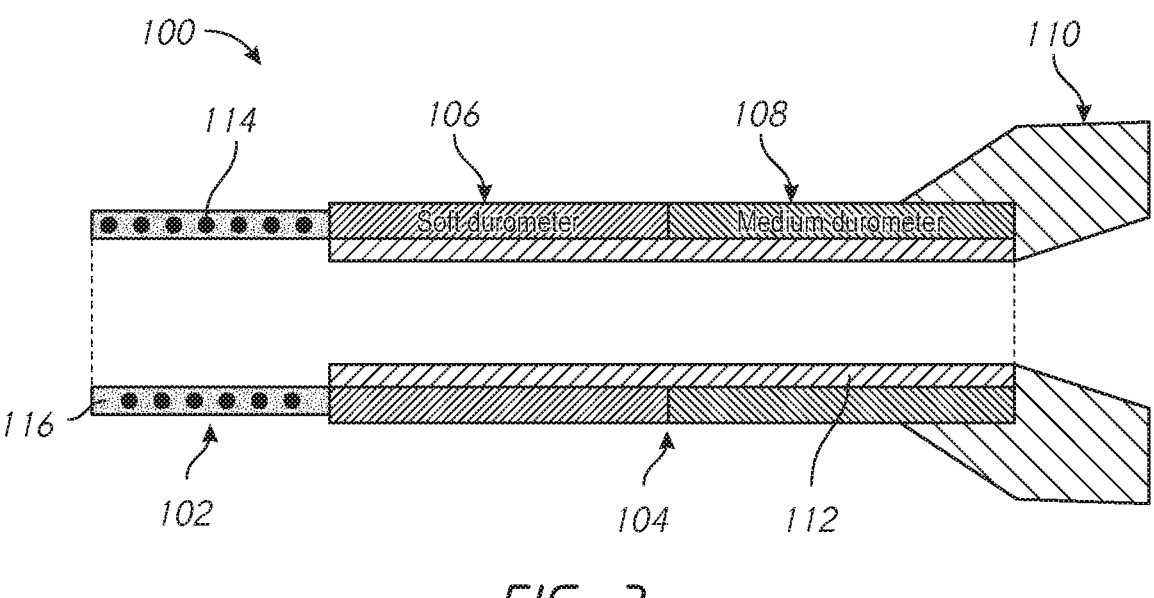
FIG. 3 is a schematic representation of the catheter shown in FIG. 2.
FIG. 4 shows a distal portion of another catheter having a single reinforcement structure.

FIG. 2 depicts a distal portion 102 of a catheter 100 having a reinforcement structure (sometimes referred to herein as an annular support) encapsulated in a fibrous coating. FIG. 3 schematically illustrates the catheter 100 including the distal portion 102 of the catheter shown in FIG. 2 and a proximal portion 104. The proximal portion 104 can include one or more sections (e.g., one, two, three, or more) of polymer tubing 106, 108. When the proximal portion 104 has multiple sections 106, 108, each section 106, 108 can have a different diameter that generally increases in the proximal direction toward the hub 110. The distal-most section 106 of the proximal portion 104 can be generally stiffer than any portion of the distal portion 102. The proximal portion 104 may or may not have a liner 112 positioned radially inward of the one or more sections 106, 108.

The catheter 100 can have at least one lumen. For catheters having a single lumen, an inner diameter at a proximal end of the distal portion 102 can be substantially the same as an inner diameter at a distal end of the proximal portion 104. In some configurations, an inner diameter of the catheter 100 can be substantially the same along the entire length of the catheter.

At least the distal portion 102 can include a reinforcement structure 114. In FIGS. 2 and 3, the reinforcement structure 114 is a coil, but in other implementations, can be a mesh, braided structure, laser cut structure, parallel spaced apart rings, helical z patterns, diamond patterns, or other structure capable of providing column strength and radial strength. The reinforcement structure 114 can include a medical grade metal material, such as nitinol, stainless steel, or otherwise, or a polymeric material, such as PEEK, Kevlar, carbon fiber filaments, or otherwise. Although the illustrated embodiment includes a single reinforcement structure 114 at a distal portion 102 of the catheter 100, additional reinforcement structures 114 may be added, for example, radially inward and/or radially outward of a coating 116, and/or the reinforcement structure 114 can form at least a part of the proximal portion 104 of the catheter 100 or extend along the entire length of the catheter 100.

At least the distal portion of the reinforcement structure 114 can be coated with a coating such as fibrous coating 116. The coating 116 can be applied to an inner and/or outer surface of the reinforcement structure 114 using an electro-spinning process. The fibrous coating 116 can be formed from a thermoplastic fluoropolymer. Exemplary materials for the fibrous coating 116 can include, but are not limited to, PTFE, PET, silicone, latex, TecoThane, nylon, PET, Carbothane (Bionate), SIBS, TecoFlex, Pellethane, Kynar, and PGLA. The fibrous nature of the coating 116 allows the catheter to stretch, which imparts flexibility. Preferably the coating remains impermeable at least to erythrocytes, or is completely fluid impermeable in the vascular environment. Although the illustrated embodiment includes a coating 116 at a distal portion 102 of the catheter 100, the coating 116 can extend at least partially into the proximal portion 104 of the catheter 100 or along the entire length of the catheter 100.

The reinforcement structure 114 can also be coated or embedded in a non-electrospun membrane such as a tubular hydrogel. For example, the reinforcement structure can be spray coated, dip coated or otherwise provided with a thin, highly flexible layer of a methacrylate polymer such as poly(HEMA), preferably in such a way that the coating is strongly adherent, e.g., there is no detachment of the coating from the underlying coil surface. Other hydrophilic and non-hydrophilic polymeric coating materials may alternatively be used, such as those obtained by polymerization of monomers selected from hydroxyethoxyethyl methacrylate (HEEMA), hydroxydiethoxyethyl methacrylate (HDEEMA), methoxyethyl methacrylate (MEMA), methoxyethoxyethyl methacrylate (MEEDA), metoxydi-ethoxyethyl methacrylate (MDEEMA), ethylene glycol dimethacrylate (EGDMA) and mixtures thereof. These polymeric coatings can be crosslinked or non-crosslinked depending upon the desired performance. These polymeric materials can be copolymers, terpolymers or even more complex macromolecular systems, or physical blends. Adherence of the methacrylate polymer biomaterial to the metallic surface of the supporting coil may be enhanced by the application of a binder polymer layer. One such binder is poly(ethersulfone). Additional details may be found in US patent Publication 2002/0065551 entitled Method for Immobilizing poly(HEMA) on Stents, to Koole, et al., which is hereby incorporated by reference in its entirety herein.

Electrospinning refers generally to processes involving the expulsion of flowable material from one or more orifices, and the material forming fibers are subsequently deposited on a collector. Examples of flowable materials include dispersions, solutions, suspensions, liquids, molten or semi-molten material, and other fluid or semi-fluid materials. In some instances, the rotational spinning processes are completed in the absence of an electric field. For example, electrospinning can include loading a polymer solution or dispersion, including any of the materials described below, into a cup or spinneret configured with orifices on the outside circumference of the spinneret. The spinneret is then rotated, causing (through a combination of centrifugal and hydrostatic forces, for example) the flowable material to be expelled from the orifices. The material may then form a "jet" or "stream" extending from the orifice, with drag forces tending to cause the stream of material to elongate into a small diameter fiber. The fibers may then be deposited on a collection apparatus. Further information regarding electrospinning can be found in U.S. Publication No. 2013/0190856, filed Mar. 13, 2013, and U.S. Publication No. 2013/0184810, filed Jan. 15, 2013, which is incorporated by reference in its entirety herein.

The catheter 100 can be formed by taking a mandrel having a diameter of the desired inner diameter of the catheter 100. Several layers of the coating 116 can be spun over the mandrel, and then the reinforcement structure 114 can be positioned over the spun material. Thereafter, another several layers of coating 116 can be spun over the reinforcement structure 114 such that the reinforcement structure 114 is encapsulated within the coating 116. The outer layers of coating 116 can fill in the interstitial spaces in the reinforcement structure 114, such as between the bends in a coil.

The fibrous encapsulated reinforcement structure allows for a catheter construction in which the region of greatest flexibility is provided over a greater length than traditional catheters. Unlike traditional catheters in which a durometer of the plastic matrix transitions a few centimeters from the distal end, the coating 116 described herein can have a generally uniform stiffness (e.g., by providing a generally constant thickness, and/or density) along a length of the distal portion 102 or along an entire length of the coating 116. The length of generally uniform stiffness can be at least about 1.0 cm, at least about 2.0 cm, at least about 4.0 cm, at least about 5.0 cm, at least about 10.0 cm, at least about 15.0 cm, at least about 20.0 cm, at least about 50.0 cm, or an entire length of the catheter.

As mentioned above, in conventional catheter designs, the coating on the outside curve stretches while the coating on the inside curve compresses, which can result in kinking. The fibrous encapsulated reinforcement structure mitigates kinking seen in larger diameter catheters having an outer diameter of at least about 5.0 F, such as between about 6.0 F and about 12.0 F, between about 8.0 F and 10.0 F, or otherwise, because the coating generally demonstrates better stretch and compression than conventional plastic catheter jacketing materials. Larger diameter catheters can be useful to ease the passage of other devices through a lumen of the catheter or to provide greater aspiration forces for a given aspiration pressure. It should be noted that this construction could be applied to any catheter diameter, including catheter diameters less than about 5.0 F or greater than about 12 F.

FIG. 4 depicts a catheter 200 with a reinforcement structure extending along a length of the catheter. The distal portion 202 can be coated with a fibrous coating as described above. The coating can transition from the fibrous coating at the distal portion 202 to a polymer tubing at the proximal portion 204 at transition point e.

The stiffness of the coating can be varied along the length of the distal portion 202 by changing the coating density or varying a thickness of the coating or the coating material. The thickness of the coating can be varied between 0.1 mm and 1 mm to change the stiffness and permeability of the covering. For example, the distal portion 202 can have multiple sections (e.g., two, three, four, or more) of varying stiffness that are separated by transition points a, b, c, d. A stiffness of the coating generally increases in the proximal direction toward the proximal portion 204 of the catheter 200. A length of the coating can have a generally uniform stiffness, thickness, and/or density. The length of generally uniform stiffness, thickness, and/or density can be at least about 1.0 cm, at least about 2.0 cm, at least about 4.0 cm, at least about 5.0 cm, at least about 10.0 cm, at least about 15.0 cm, at least about 20.0 cm, at least about 50.0 cm, an entire length of the catheter, or otherwise. This length of uniform coating may be measured from a distal end of the catheter 200.

Dual Reinforcement Structure

Figures 5, 6:
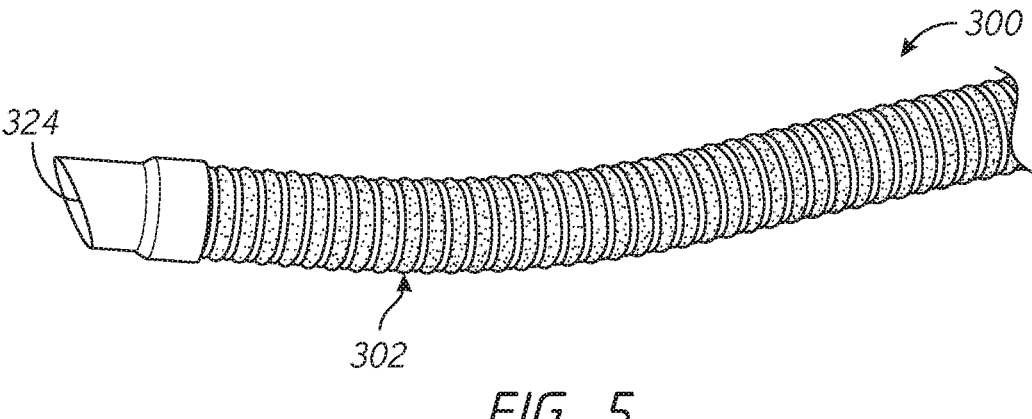
FIG. 5 shows a distal portion of a catheter having two reinforcement structures.
FIG. 6 is a schematic representation of the catheter shown in FIG. 5.

FIG. 5 shows a distal portion 302 of a catheter 300 having two reinforcement structures (sometimes referred to herein as annular supports) separated by a tubular membrane. FIG. 6 schematically illustrates a catheter 300 including the distal portion 302 of the catheter shown in FIG. 5 and a proximal portion 304. The distal portion 302 and the proximal portion 304 can have a same inner diameter. The proximal portion 304 can include one or more sections 306, 308 (e.g., one, two, three, or more) of polymer tubing each having a different durometer. When the proximal portion 304 has multiple sections 306, 308, the durometer of each section 306, 308 can increase in the proximal direction toward the hub 310. The distal-most section 306 of the proximal portion 304 is generally stiffer than any portion of the distal portion 302. The proximal portion 304 may or may not have a liner 312 positioned radially inward of the one or more sections 306, 308. Providing a catheter 300 without a liner 312 in the distal portion 302 of the catheter 300 increases the flexibility in the distal portion 302 compared to conventional catheters.

At least the distal portion 302 can include an outer reinforcement structure 318 and an inner reinforcement structure 314. For example, in FIGS. 5 and 6, the reinforcement structures 318, 314 are helical-shaped support structures (e.g., round wire coils or flat wire coils). The pitch of one or both of the helical-shaped support structures can be between about 0.01 inches to about 0.03 inches, between about 0.015 inches and about 0.25 inches, or otherwise. The reinforcement structures 318, 314 can include a medical grade metal material, such as nitinol, stainless steel, or otherwise, or a polymeric material, such as PEEK, Kevlar, carbon fiber filaments, or otherwise. Although the preferred embodiment of the reinforcement structures is a helical wire, other similar embodiments could include a mesh, braided structure, laser cut structure, parallel spaced apart rings, helical z patterns, laser cut diamond patterns, or other structure capable of providing column strength and radial strength.

As shown in FIG. 6, the tubular membrane 316 can have a helical convoluted or corrugated structure having a plurality of radially outwardly projecting helical ribs 320 on the outer surface of the tubular membrane 316 and a plurality of radially inwardly projecting helical ribs 322 on the inner surface of the tubular membrane 316 (or viewed another way helical grooves on inner and outer surfaces of the tubular membrane 316).

In some embodiments, the tubular membrane 316 can be constructed from an inelastic plastic material (e.g., PTFE), but even when the tubular membrane 316 is inelastic, the corrugations provide flexibility in an otherwise stiff tubular member 316. When the distal portion 302 of the catheter 300 bends, flexibility is primarily provided by the unfolding of the corrugations on the outer bend and folding of the corrugations on the inner bend, not stretching. Other exemplary materials for the tubular membrane 316 can include, but are not limited to, expanded PTFE (ePTFE), electrospun PTFE, PET, silicone, latex, TecoThane, nylon, PET, Carbothane (Bionate), SIBS, TecoFlex, Pellethane, Kynar, and PGLA.

The formation of an organized corrugated wall structure during bending provides flexibility while reducing the likelihood of kinking. As the catheter shaft is bent, the amplitude of the corrugations on the outer bend 316a decreases and the amplitude of the corrugations on the inner bend 316b increases (see FIG. 7A). Further, as the catheter shaft is bent, the wavelength $\lambda_1$ of the corrugations on the inner bend 316b decreases (see FIG. 7B) and the wavelength $\lambda_2$ of the corrugations on the outer bend 316a increases (see FIG. 7C). In a bent configuration, the average wavelength of the corrugations on the inner bend 316b can be less than the average wavelength of the corrugations on the outer bend 316a, and the average amplitude of the corrugations on the inner bend 316b can be greater than the average amplitude of the corrugations on the outer bend 316a.

Figure 7A:
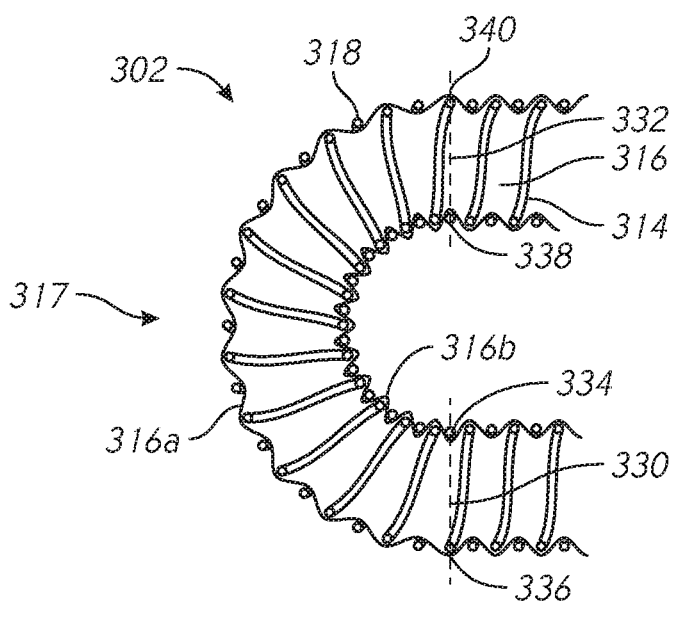
FIG. 7A is a schematic representation of a cross-section of the distal portion of the catheter shown in FIG. 5 in a bent configuration.

Referring to FIG. 7A, a reference line 330 may be drawn perpendicular to a longitudinal axis of the catheter shaft, such that it crosses the tubular wall at a first point 334 and a second point 336. A second reference line 332, spaced apart from the first reference line 330 also resides perpendicular to the longitudinal axis of the catheter, and crosses the wall at a first point 338 and a second point 340. When the catheter is oriented linearly, first reference line 330 is parallel to and spaced apart from the second reference line 332.

The distance between reference points 334 and 338 is equal to the distance 336-340, when the catheter is in a linear configuration. As shown in FIG. 7A, the distance 334-338 (inside length) is less than the distance 336-340 (outside length), when the catheter is in a curved configuration.

Figure 7B:
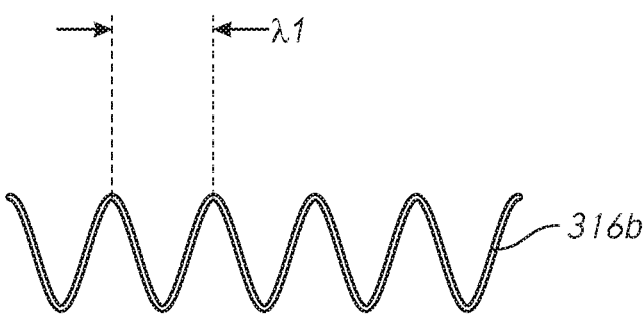
FIG. 7B schematically illustrates an inner bend of the distal portion shown in FIG. 7A.
Figure 7C:
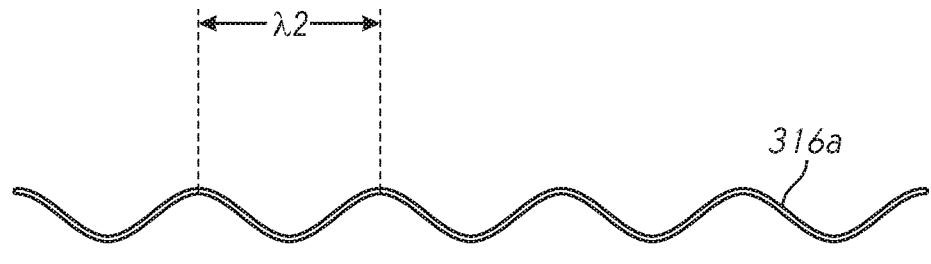
FIG. 7C schematically illustrates an outer bend of the distal portion shown in FIG. 7A.

Due to the significant axial compression and expansion of the sidewall of catheters built in accordance with the present disclosure, the catheter shaft can be wrapped into a relatively tight radius bend without kinking. For example, a catheter shaft having an OD of at least about 0.05 inches or 0.1 inches or greater may be bent such that the outside length is at least about 200% and in some constructions at least about 300% or 400% of 500% or more the inside length. Axial compression of the wall along the inside length is accomplished by decreasing the wavelength between adjacent ribs along the inside length as shown in FIG. 7B, and/or increasing the wavelength between adjacent ribs along the outside length as shown in FIG. 7C.

Catheters having an outside diameter of at least about 0.05 inches, in some implementations at least about 0.08 inches, or 0.1 inches or 0.2 inches or more can be bent around a radius of curvature for the inside length of less than about 0.075 inches, and in some embodiments less than about 0.05 inches, 0.04 inches, or 0.025 inches or less, without kinking.

In some implementations of the catheter shaft, a catheter having an OD of at least about 0.05" (e.g., 0.066"), or at least about 0.1" (e.g., 0.111") can have an OD to kink radius ratio of at least about 2.0, or 2.5 or 3.0 or 3.5 or more. Kink radius is the radius at the point when kinking first occurs, so bending the catheter shaft around the kink radius or a smaller radius will cause a kink in the catheter shaft.

The corrugations permit the catheter shaft to assume a relatively tight radius of curvature without kinking or stressing the plastic tubular membrane in either stretch or compression. The combination of corrugations and helical reinforcement structures 314, 318 produces a catheter shaft with ideal properties that are normally in competition, e.g., flexibility with high resistance to compression or kinking, because the reinforcement structures 314, 318 provide support to and facilitate alignment of the of the corrugations in the tubular membrane 316. When the distal portion 302 of the catheter bends, an arcuate portion 317 of the bend hinges in a generally uniform manner so that the catheter does not buckle or kink in any single position. For example, for a catheter 300 having an outer diameter of less than or equal to about 5.0 F, the distal portion 302 will not kink when bent to form an arcuate portion 317 having a radius (measured from the inner curvature) of no more than about 0.01 inches, no more than about 0.015 inches, no more than about 0.02 inches, no more than about 0.25 inches, or no more than about 0.3 inches. As another example, for a catheter 300 having an outer diameter of less than or equal to about 8.0 F, the distal portion 302 will not kink when bent to form an arcuate portion 317 having a radius (measured from the inner curvature) of no more than about 0.4 inches or no more than about 0.5 inches.

The pitch of the inner groove of the tubular membrane 316 can be approximately the same as the pitch of the inner reinforcement structure 314, and the pitch of the outer groove of the tubular membrane 316 can be approximately the same as the pitch of the outer reinforcement structure 318. The depth of the inner groove can be at least about 1× and often between about 1.5× and 2.0× a radial dimension such as a diameter of the wire forming the inner reinforcement structure 314, and the depth of the outer groove can be between about 1.5× and 2.0× a radial dimension such as a diameter of the wire forming the outer reinforcement structure 318. If the reinforcement structures were rings instead of helices, the tubular membrane would have a recurring series of ring-like corrugations rather than a helical pattern.

The outer reinforcement structure 318 can be positioned in the outer helical groove such that the helical rib 320 extends through the interstitial spaces of the adjacent outer reinforcement structure 318. The inner reinforcement structure 314 can be positioned in the inner helical groove such that the helical rib 322 extends through the interstitial spaces of the second reinforcement structure 318. With this design, both the inner and outer surfaces of the distal portion 302 of the catheter 300 are textured, which can decrease resistance when the outer surface of the catheter contacts a vessel wall.

The inner diameters of the outer and inner reinforcement structures 318, 314 can differ from each other, e.g., by at least about 0.001 inches (or at least about 0.005 inches) and/or by less than a diameter of the wire forming the reinforcement structures 318, 314. The diameter of the wires can be larger than wires in conventional catheters because the reinforcement structures 318, 314 do not need to be fully encased in a plastic matrix. For example, the diameter of the wires can be between about 0.003 inches and about 0.007 inches, such as between about 0.004 inches and about 0.005 inches in a catheter intended for neurovascular access. The larger diameter wire provides greater hoop strength, crush resistance, and kink resistance than traditional construction techniques.

In some implementations, the outer reinforcement structure 318 can have a smaller inner diameter than at least an outer diameter or an inner diameter of the inner reinforcement structure 314. The inner diameter of the inner reinforcement structure 314 can be at least about 1% greater than, at least about 2% greater, or at least about 5% greater than an inner diameter of the outer reinforcement structure 318. For example, in a 9.0 F catheter, the outer reinforcement structure 318 can have an inner diameter of 0.100 inches and the inner diameter of the inner reinforcement structure 314 can have an inner diameter of 0.105 inches. With this configuration, the inner reinforcement structure 314 presses upward or outward on the tubular membrane 316 and the outer reinforcement structure 318 presses inward on the tubular membrane 316 to retain the assembled configuration of the catheter 300. This configuration also creates deeper grooves in the tubular membrane 316 such that there is a greater length of the tubular membrane 316 (e.g., greater arc length or greater length when flattened) between adjacent bends in either reinforcement structure 318, 314. The deeper corrugations provide more flexibility.

At least one of the reinforcement structures 318, 314 is not encapsulated in the tubular membrane 316. Rather, at least one or both of the reinforcement structures 318, 314 floats with respect to the tubular membrane 316. Unlike conventional catheters, the reinforcement structures 318, 314 are floating (e.g., not fully encapsulated and/or joined to the tubular membrane 316), so the flexibility of reinforcement structures 318, 314 is preserved without negatively affecting the wall thickness and overall size of the catheter. This increased flexibility enables the use of a larger overall diameter catheter to perform the same tasks that are typically performed using a smaller diameter catheter. It should be understood that corrugation of the tubular membrane would increase the catheter shaft flexibility whether or not the reinforcement structures are floating with respect to the tubular membrane or encapsulated by the tubular membrane, but when the reinforcement structures are floating with respect to the tubular membrane, the catheter may have greater flexibility and trackability.

When the portion of the catheter 300 having the above-described construction is flexed, each groove or pleat on an outer curve of the bent catheter 300 flexes outward a few degrees (e.g., one degree, two degrees, three degrees, or more) to accommodate the change in geometry. Since the reinforcement structures 318, 314 are not encapsulated in a plastic matrix, there is very little energy needed to bend the catheter 300 compared to conventional catheters.

This type of catheter construction allows for a catheter in which the region of greatest flexibility is provided over a greater length than traditional catheters. Unlike traditional catheters in which a durometer of the plastic matrix transitions a few centimeters from the distal end, the distal portion 302 can have a generally uniform stiffness profile along a length of the distal portion 302, or over at least a length of at least about 1.0 cm, at least about 2.0 cm, at least about 4.0 cm, at least about 5.0 cm, at least about 10.0 cm, at least about 15.0 cm, at least about 20.0 cm, at least about 50.0 cm, or an entire length of the catheter. The length of uniform stiffness can be measured from a distal end of the catheter. Compared to conventional catheters, there are fewer transition points between sections of varying stiffness, which reduces the number of transition points that are prone to kinking.

The distal portion 302 of the catheter can be mated to the proximal portion 306 of the catheter in a butt joint. Alternatively, as described in further detail below, one or more of the tubular membrane 316, outer reinforcement structure 318, and the inner reinforcement structure 318 can extend into a proximal portion 304 of the catheter 300 to join the distal portion 302 and the proximal portion 304 and reduce the likelihood of kinking at the connection.

The proximal end of the inner reinforcement structure 314 can be encapsulated in the polymer tubing of the proximal portion 304, e.g., in the distal-most or softest durometer section 306. The proximal end of the outer reinforcement structure 318 can be encapsulated in the same section of tubing 306 or extend proximally toward the hub 310 within the walls of the polymer tubing 306, 308 or radially outward of the polymer tubing 306, 308. The distal ends of the inner and outer reinforcement structures 314, 318 can be encapsulated in a polymer jacket that may be separate from the tubular membrane 316. Polymer jacketing material may be bonded to one or more parts of the distal portion 302 to improve kink resistance.

FIG. 6 schematically illustrates the tubular membrane 316 only extending along a length of the distal portion 302 and/or a length of the reinforcement structures 318, 314. However, in other configurations, the tubular membrane 316 and/or the coils may extend proximally of the distal portion 302 by at least about 1 cm or 5 cm or 10 cm or more in a proximal direction from the proximal end of the distal portion 302. For example, the tubular membrane 316 may form at least part of or the entirety of the liner 312 of the proximal portion 304. The tubular membrane 316 and/or the coils can have a thickness of less than or equal to about 0.01 inches or less than or equal to about 0.001 inches. The tubular membrane 316 can be constructed from a polymer such as PTFE, ePTFE, electrospun PTFE, silicone, latex, TecoThane, nylon, PET, Carbothane (Bionate), SIBS, Teco-Flex, Pellethane, PGLA, or Kynar.

The properties of the dual reinforcement structure design are generally insensitive to catheter diameter, thus the design can be applied to larger diameter catheters having an outer diameter of at least about 5.0 F and/or less than or equal to about 12.0 F, between about 8.0 F and 10.0 F. Larger diameter catheters can be useful to ease the passage of other devices through a lumen of the catheter or to provide greater aspiration forces for a given aspiration pressure. It should be noted that this construction could be applied to any catheter diameter, including catheter diameters less than 5.0 F or greater than 12.0 F.

Although the schematic illustration in FIG. 6 shows the distal tip 324 being cut perpendicular to the longitudinal axis of the catheter, in other configurations, the distal tip 324 can be cut at an oblique angle to the longitudinal axis of the catheter (as shown in FIG. 5) to facilitate trackability at bifurcations. For aspiration catheters, the beveled tip can increase a surface area at the distal end 324 for engaging the clot, thus increasing total suction force on a surface such as an embolus. The beveled tip may also prevent the clot from clogging the catheter by creating a larger end hole through which an embolus can pass. In some configurations, the distal tip may be a soft, flexible tip to create a seal against the emboli surface. In some configurations, the distal tip 324 may have a feature (e.g., offset channel or lumen) to force the guidewire to one side of the distal opening to facilitate trackability.

Although not shown, the construction at the distal portion 302 of the catheter may extend along an entire working length of the catheter 300. A durometer of the reinforcement structures 318, 314 and/or the tubular membrane 316 can generally increase in the proximal direction to provide the desired stiffness profile.

One method of forming the catheter 300 is to first form the individual components. To form the corrugations in the tubular membrane, the tubular membrane 316 can be positioned on a mandrel having a helical groove and a tensioned wire can be positioned on top of the tubular membrane 316 to force portions of the membrane into the groove in the mandrel. The tubular membrane 316 can be heat set to fix the corrugations in the tubular membrane 316. To form the reinforcement structures 314, 318, wires can be wrapped around mandrels having the desired inner diameter of the respective reinforcement structure 314, 318 and heat set. The final assembly is formed by mating the two reinforcement structures 314, 318 with the respective grooves in the tubular membrane 316. With the inner reinforcement structure 314 positioned on a mandrel, the tubular membrane 316 can be wound over the inner reinforcement structure 314. Next, the outer reinforcement structure 318 can be wound around the groove in the outer surface of the tubular membrane.

Figure 8:
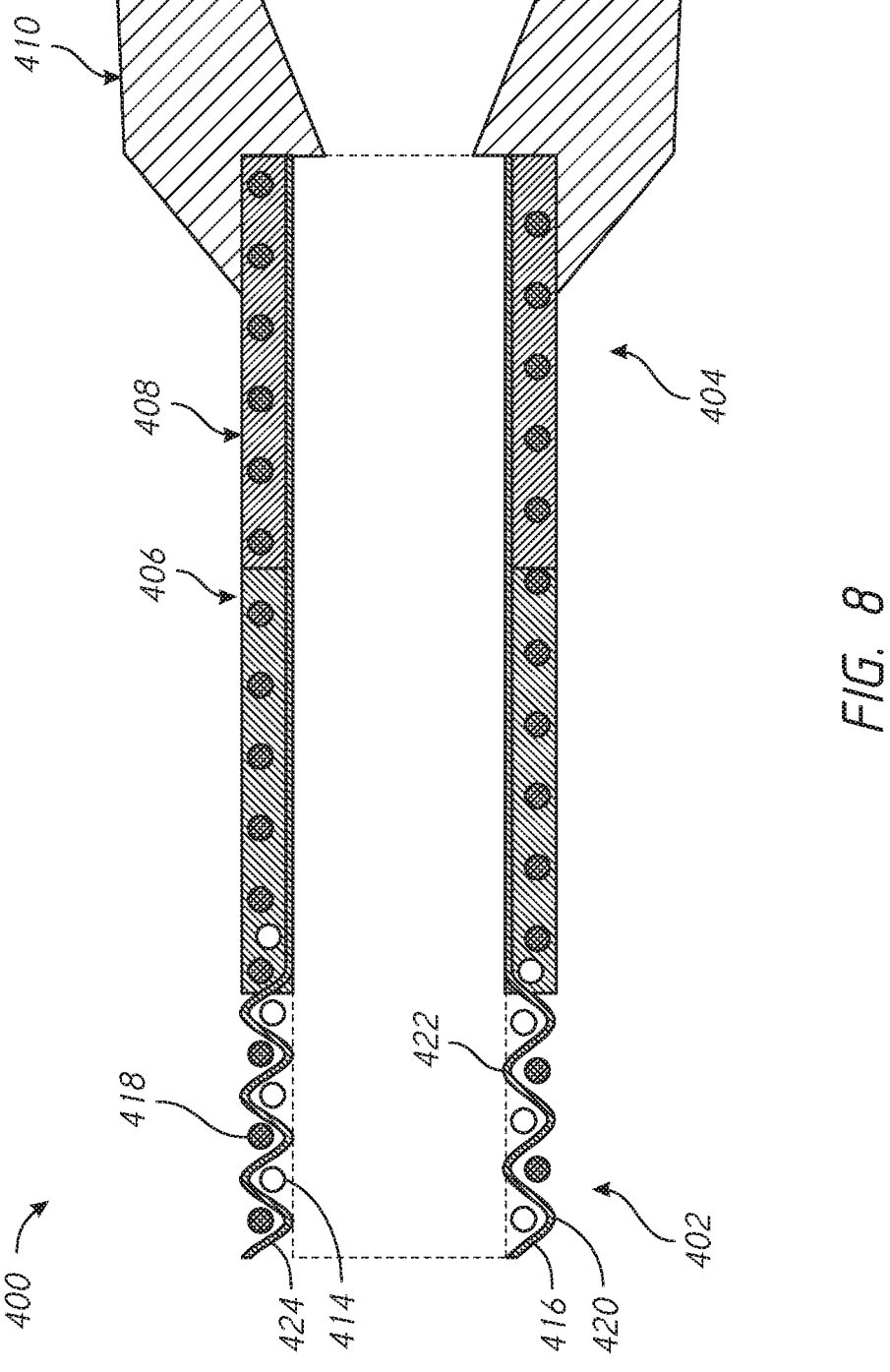
FIG. 8 is a schematic representation of another catheter having two reinforcement structures.

FIG. 8 illustrates another catheter 400 having dual reinforcement structures. The distal portion 402 resembles or is identical to the distal portion 302 discussed above in many respects. Accordingly, numerals used to identify features of the catheter 300 are incremented by a factor of one hundred (100) to identify like features of the catheter 400. Any component or step disclosed in this embodiment can be used in other embodiments described herein.

As mentioned above, the inner and/or outer reinforcement structure 314, 318 can extend proximally of the distal portion 302 to provide support to the proximal portion 304 (e.g., to prevent kinking). For example, as shown in FIG. 7, the outer reinforcement structure 418 can provide the proximal support and extend along a length of catheter 400. The outer reinforcement structure 418 can be encapsulated in the one or more sections of polymer tubing 406, 408. The inner reinforcement structure 414 can terminate within a distal section 406 of the proximal portion 404. For example, a proximal end of the inner reinforcement structure 414 can extend through a thickness of the tubular membrane 416 and into a wall of the distal-most section of polymer tubing 406. In this configuration, the proximal ends of both reinforcement structures 418, 414 can be fully encapsulated in the polymer tubing 406, 408 forming the proximal portion 404.

In other configurations, the inner reinforcement structure 414 can provide the proximal support and extend along at least a partial or entire length of the proximal portion 404. The inner reinforcement structure 414 can be encapsulated in the one or more sections of polymer tubing 406, 408. The outer reinforcement structure 418 can terminate in a wall of the polymer tubing at the distal-most section 406 of the proximal portion 406 or be positioned radially outward of the proximal portion 406 and extend along at least a partial or entire length of the proximal portion 406.

Single Reinforcement Structure Affixed to Tubular Membrane

Figure 9:
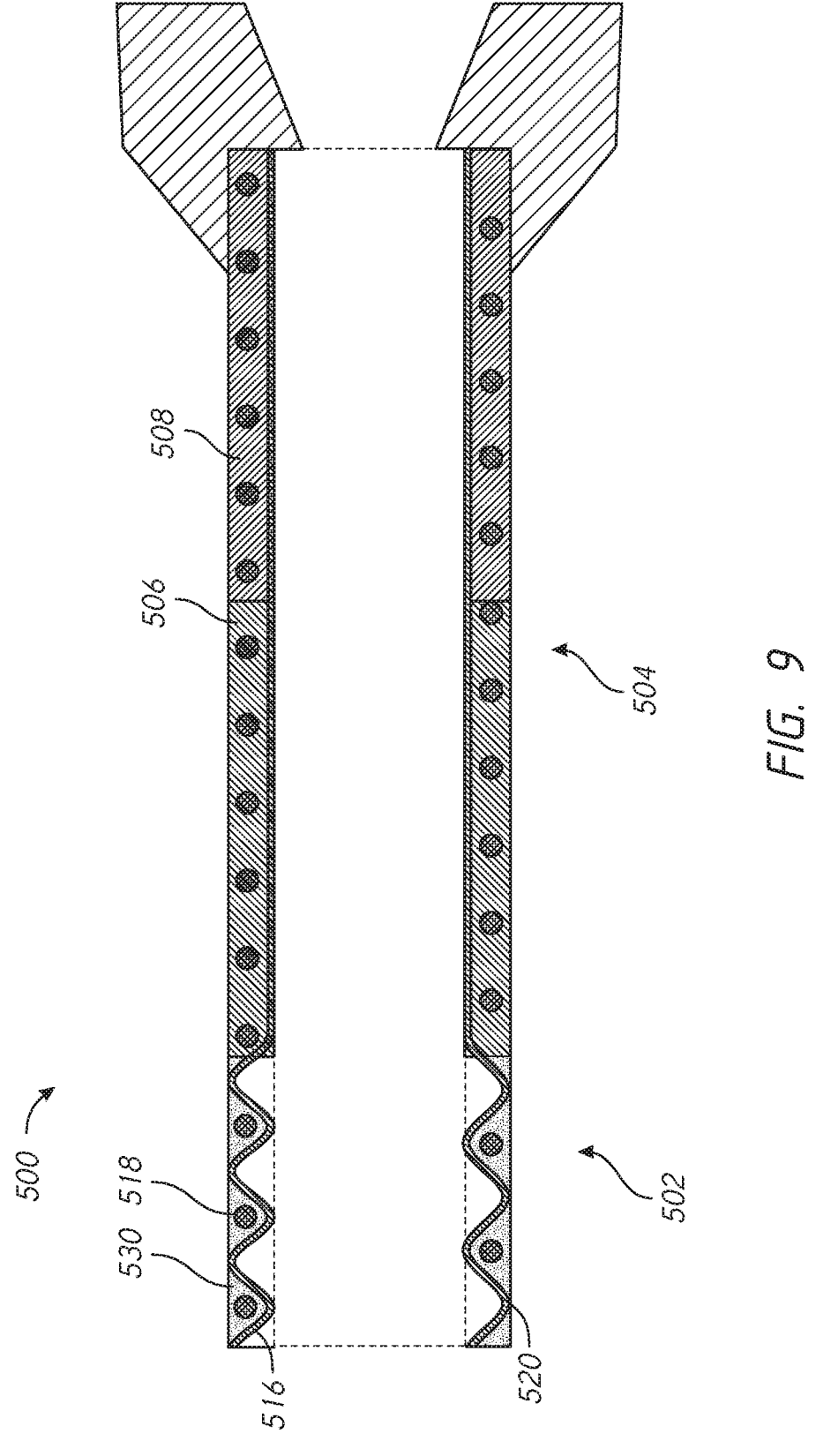
FIG. 9 is a schematic illustrate of yet another embodiment of a catheter having a single reinforcement structure.

FIG. 9 illustrates another embodiment of a catheter with a single reinforcement structure 518 (sometimes referred to herein as an annular support). At least a distal portion 502 of the catheter 500 can include a reinforcement structure 518 and a tubular membrane 516. As shown in FIG. 9, the reinforcement structure 518 is on an outer surface of the tubular membrane 516, but in other configurations, the reinforcement structure 518 could be positioned on an inner surface of the tubular membrane 516.

The reinforcement structure 518 can be a helical-shaped support structures (e.g., a round wire coil or flat wire coil). The pitch of the helical-shaped support structures can be between about 0.01 inches to about 0.03 inches, between about 0.015 inches and about 0.25 inches, or otherwise. The reinforcement structure 518 can include a medical grade metal material, such as nitinol, stainless steel, or otherwise, or a polymeric material, such as PEEK, Kevlar, or carbon fiber filaments, or otherwise. Although the preferred embodiment of the reinforcement structures is a helical wire, other similar embodiments could include a mesh, braided structure, laser cut structure, diamond patterns, parallel spaced apart rings, helical z patterns, or other structure capable of providing column strength and radial strength rings.

The tubular membrane 516 can have a helical convoluted, pleated, or corrugated structure having a helical rib 520 on the outer surface of the tubular membrane 516. The tubular member 516 can be inelastic and constructed from a polymer material (e.g., PTFE), but even when the tubular membrane 516 is inelastic, the corrugations provide flexibility. The corrugations permit the catheter 500 to assume a relatively tight radius of curvature without kinking or stressing the plastic tubular membrane in either stretch or compression. The properties of the corrugated structure are generally the same as the corrugated structure described above with respect to FIGS. 7A-7C. Other exemplary materials for the tubular membrane 516 can include, but are not limited to, ePTFE, electrospun PTFE, PET, silicone, latex, TecoThane, nylon, PET, Carbothane (Bionate), SIBS, Teco-Flex, Pellethane, Kynar, and PGLA.

The pitch of the outer groove of the tubular membrane 516 can be approximately the same as the pitch of the reinforcement structure 518. The depth of the outer groove can be between about 1.5x and 2.0x a diameter of the wire forming the outer reinforcement structure 318. If the reinforcement structure 518 has rings instead of helices, the tubular membrane 516 would have a recurring series of ring-like corrugations rather than a helical pattern.

The reinforcement structure 518 can be positioned in the outer helical groove such that the helical rib 520 extends through the interstitial spaces of the reinforcement structure 518. The corrugations on the inner and outer surfaces of the distal portion 502 of the catheter 500 provide texturing, which can decrease resistance when the outer surface of the catheter contacts a vessel wall.

The reinforcement structure 518 can be affixed to the tubular membrane 516 by a thin polymer coating 530 (e.g., a Kynar or urethane coating). The coating may be applied using a spray coating technique. The thickness for the coating 530 can be less than or equal to about 0.01 inches, less than or equal to about 0.001 inches, or less than or equal to about 0.0005 inches. For example, the coating can be sprayed over the assembled catheter 500, such that the coating 530 fills the spaces between the reinforcement structure 518 and the surface of the tubular membrane 516. Although, in other configurations, the reinforcement structure 518 could be floating with respect to the tubular membrane 516 as described with respect to catheter 300.

Similar to the catheter 300, when the distal portion 502 of the catheter 500 bends, an arcuate portion of the bend hinges in a generally uniform manner so that the catheter does not buckle or kink in any single position. The reinforcement structure 518 promotes and supports the uniform hinging of the tubular membrane 516. Although the reinforcement structure 518 is affixed to the tubular membrane 516, the polymer coating 530 is sufficiently thin to not appreciably increase an overall thickness of the catheter.

As shown in FIG. 9, the reinforcement structure 518 can extend proximally of the distal portion 502 to provide support to the proximal portion 504 (e.g., to prevent kinking). For example, the reinforcement structure can provide the proximal support and extend along a length of catheter 500. The reinforcement structure 518 can be encapsulated in the one or more sections of polymer tubing 506, 508. The tubular membrane 516 can extend proximally and provide an inner lining of the proximal portion 504. In other constructions, the reinforcement structure 518 may terminate in the distal portion 502 or in a distal portion of the proximal portion 504.

Stiffness v. Outer Diameter

Figure 10:
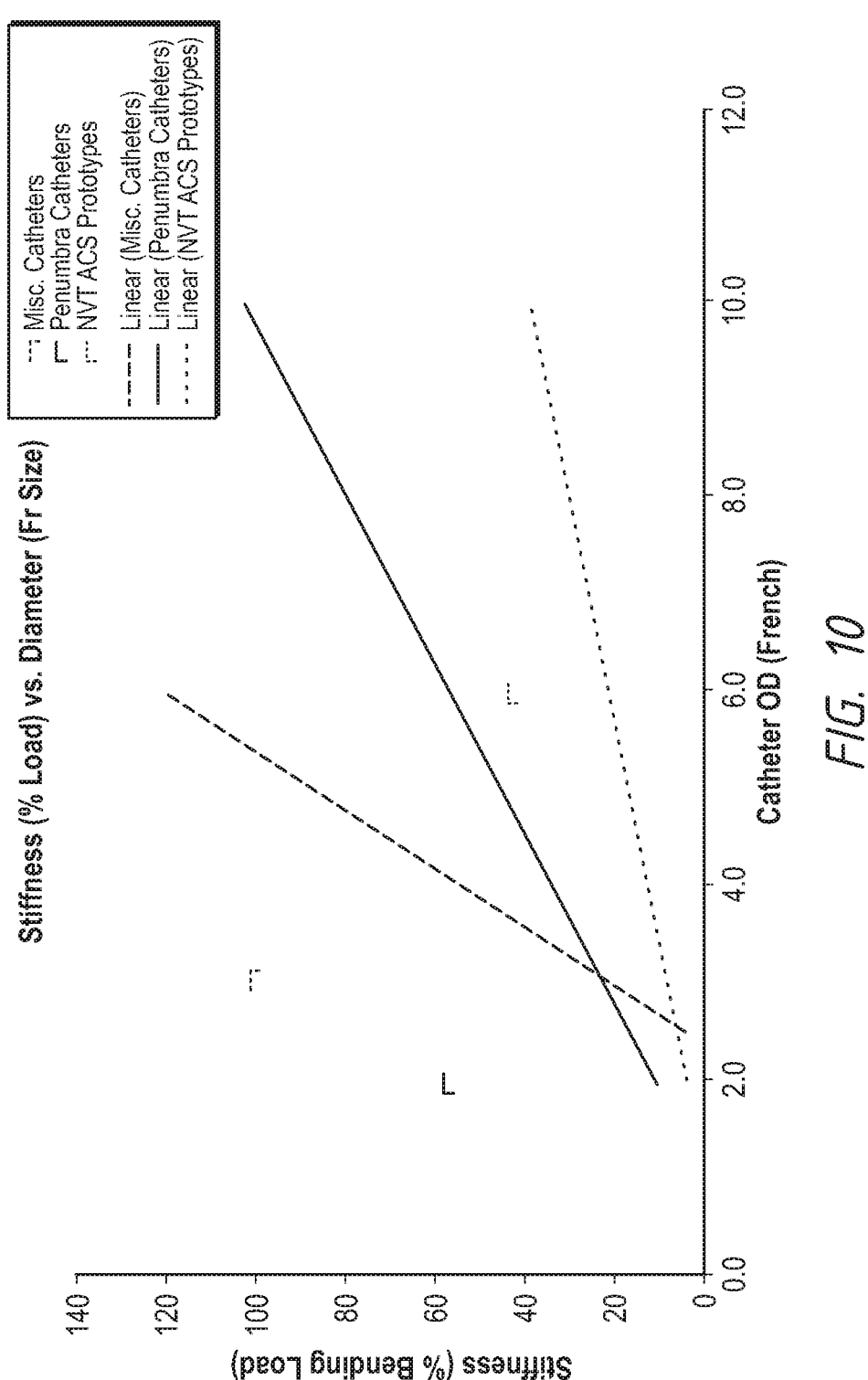
FIG. 10 is a graph of stiffness v. outer diameter for various catheter devices.

As described above, the catheter construction of the dual reinforcement structure design can provide greater flexibility than conventional catheters, particularly for larger diameter catheters. FIG. 10 is a graph showing catheter outer diameter v. stiffness for the distal portion of the dual reinforcement structure catheter described herein (e.g., catheter 300 or catheter 400) compared to the most flexible portion of other commercially available catheter designs. The stiffness of the catheter can be measured as a percentage of the bending load using an ASTM D 747 test (standard test method for apparent bending modulus of plastics by means of a cantilever beam).

As shown in FIG. 10, the stiffness of the distal portion of the dual reinforcement structure catheter is generally at least less than half of the stiffness of the most flexible portion of commercially available catheters for catheters having an outer diameter up to at least about 10.0 F. The stiffness of a distal portion of a catheter having the dual reinforcement structure design (e.g., catheter 300 or catheter 400) can have a stiffness of less than or equal to about 40% of a bending load for a catheter having an outer diameter up to and including about 10.0 F, less than or equal to about 30% of a bending load for a catheter having an outer diameter up to and including about 8.0 F, or less than or equal to about 20% of a bending load for a catheter having an outer diameter up to and including about 6.0 F. In some implementations, the stiffness of a catheter having an outer diameter of at least about 4.0 F can have a percentage bending load of no more than about 30, or no more than about 20. In some implementations, the stiffness of a catheter having an outer diameter of at least about 6.0 F can have a % bending load of no more than about 50, or no more than about 40, or no more than about 30, or no more than about 20. In some implementations, the stiffness of a catheter having an outer diameter of at least about 8.0 F can have a percentage bending load of no more than about 60, or no more than about 40, or no more than about 30. In some implementations, the stiffness of a catheter having an outer diameter of at least about 10.0 F can have a percentage bending load of no more than about 80, or no more than about 60, or no more than about 40. The outer diameter referred to above can be measured along any portion of the catheter shaft, for example, anywhere along the distal portion of the catheter shaft.

Single Floating Reinforcement Structure

FIGS. 11A-11D illustrate another embodiment of a highly flexible, kink resistant catheter 1100 having an elongate tubular body. The catheter 1100 can include a distal portion 1104, a proximal portion 1106, and a central lumen 1116. The proximal portion 1106 and/or the transition 1105 between the distal portion 1104 and the proximal portion 1106 can include any of the corresponding features of the above-described catheters.

The distal portion 1104 is more flexible than the proximal portion 1106. The distal portion 1104 can have a generally uniform stiffness profile over at least a length of at least about 1.0 cm, at least about 2.0 cm, at least about 4.0 cm, at least about 5.0 cm, at least about 10.0 cm, at least about 15.0 cm, at least about 20.0 cm, at least about 50.0 cm of the catheter, or an entire length of the elongate tubular body. The length of uniform stiffness can be measured from a distal end 1102 of the catheter 1100.

Figures 11A, 11B:
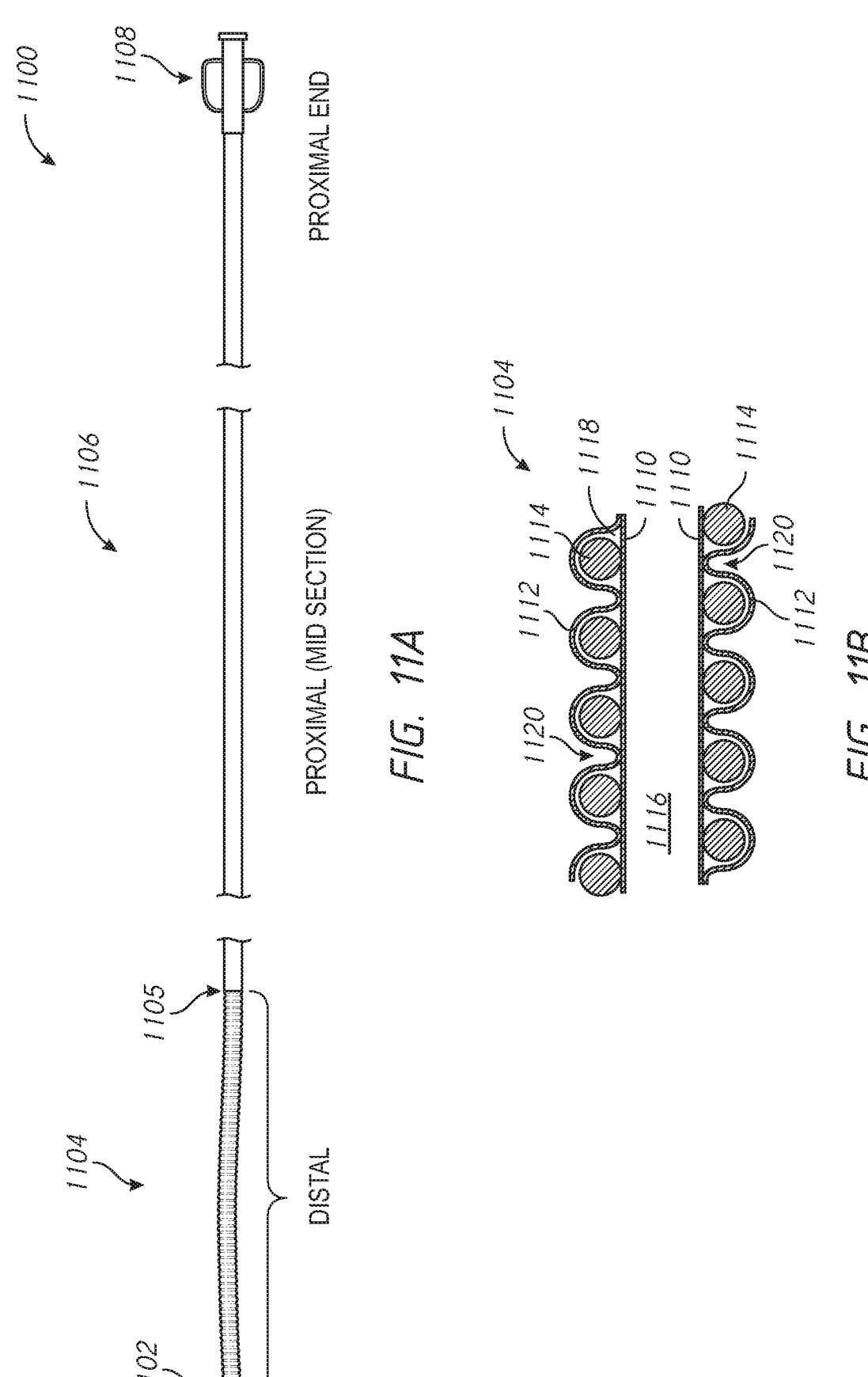
FIGS. 11A-11D illustrate yet another catheter having a single reinforcement structure.

As shown in FIG. 11B, at least the distal portion 1104 can include a helical support 1114 positioned concentrically between an inner tubular layer 1110 and an outer tubular layer 1112. The inner tubular layer 1110 can define at least a portion of the central lumen 1116 of the catheter 1100. The helical support 1114 can be carried concentrically over the inner layer 1110. Adjacent loops of the helical support 1114 can be axially spaced apart at least when the catheter 1100 is at rest. The outer tubular layer 1112 can be carried concentrically over the helical support 1114. The outer tubular layer 1112 can extend at least a length of the distal portion 1104 or the entire length of the elongate tubular body.

The inner tubular layer 1110 and the outer tubular layer 1112 are bonded together in the space 1120 between adjacent loops of the helical support 1114 to form a helical channel 1118, as shown in FIG. 11B. The helical support 1114 is floating unbonded within the helical channel 1118, e.g., the helical support 1114 is not molecularly or physically attached to the inner tubular layer 1110 or the outer tubular layer 1112. The diameter of the best fit circle corresponding to the size of the helical channel 1118 exceeds the diameter of the helical support 1114 by at least about 0.001 inches, at least about 0.0015 inches, or at least about 0.002 inches. In one implementation, no additional component, material, or fluid is provided in the space between the helical support 1114 and a wall of the helical channel 1118. Because the helical support 1114 is unbonded with respect to inner and outer tubular layers 1110, 1112, the helical support 1114 is able to move freely, which facilitates flexibility and trackability. If the catheter 1100 was cut transversely through the distal portion 1104 of the catheter 1100 to produce a catheter body segment of about 2 cm in length, the helical support 1114 could be removed by grasping a cut end of the helical support 1114 and pulling the helical support 1114 out of the helical channel 1118 non destructively, by hand.

The helical support 1114 can extend along at least a partial length (e.g., the length of the distal portion) or a full length of the catheter 1100 (e.g., from a distal tip 1102 to a proximal hub 1108). The helical support 1114 can be formed from wire (e.g., round wire or flat wire). The wire can include a medical grade metal material, such as nitinol or stainless steel, or a polymeric material, such as PEEK, Kevlar, carbon fiber filaments, or otherwise. The helical support 1114 can have a constant inner and/or outer diameter. The helical support 1114 can have a cross-section in the radial direction of no more than about 0.006 inches, or no more than about 0.005 inches, no more than about 0.004 inches, or no more than 0.003 inches. The pitch of the helical support can be between about 0.01 inches to about 0.03 inches, between about 0.01 inches to about 0.018 inches, between about 0.015 inches and about 0.25 inches, or otherwise. In some configurations, the pitch can vary over a length of the helical support 1114. For example, the helical support 1114 could have a reduced pitch at the proximal loops compared to the distal loops. The pitch may gradually increase from the proximal end toward the distal end of the helical support 1114. Although the reinforcement structure in this embodiment is a helical wire, other similar embodiments could include a mesh, helical z patterns, braided structure, laser cut structure, diamond patterns, parallel spaced apart rings, or other structure capable of providing column strength and radial strength rings.

The inner tubular layer 1110 and/or the outer tubular layer 1112 can include PTFE, ePTFE, electrospun PTFE, silicone, latex, TecoThane, nylon, PET, Carbothane (Bionate), SIBS, TecoFlex, Pellethane, PGLA, or Kynar. The inner tubular layer 1110 and/or outer tubular layer 1112 can include a thickness of no more than about 0.004 inches, or no more than about 0.002 inches. The inner and outer tubular layers 1110, 1112 in at least the distal portion 1104 can be formed from a single section of material or two different sections of similar or different material. The inner diameter and/or outer diameter of the distal portion 1102 of the catheter 1100 can be constant (e.g., a smooth surface) or vary (e.g., a corrugated surface). As shown in FIG. 11B, the distal portion 1104 can include a corrugated outer surface and a smooth inner surface. The corrugated outer surface can decrease resistance when the outer surface of the catheter contacts a vessel wall.

As explained further below, the inner tubular layer 1110 can be formed from a single segment or two different segments of material (e.g., a proximal section and a distal section). In instances where the inner tubular layer 1110 is formed from two different segments of material, the two segments can be joined by a skived joint. The two segments can be joined at the transition 1105 between the proximal portion 1106 and the distal portion 1102.

Figures 11C, 11D:
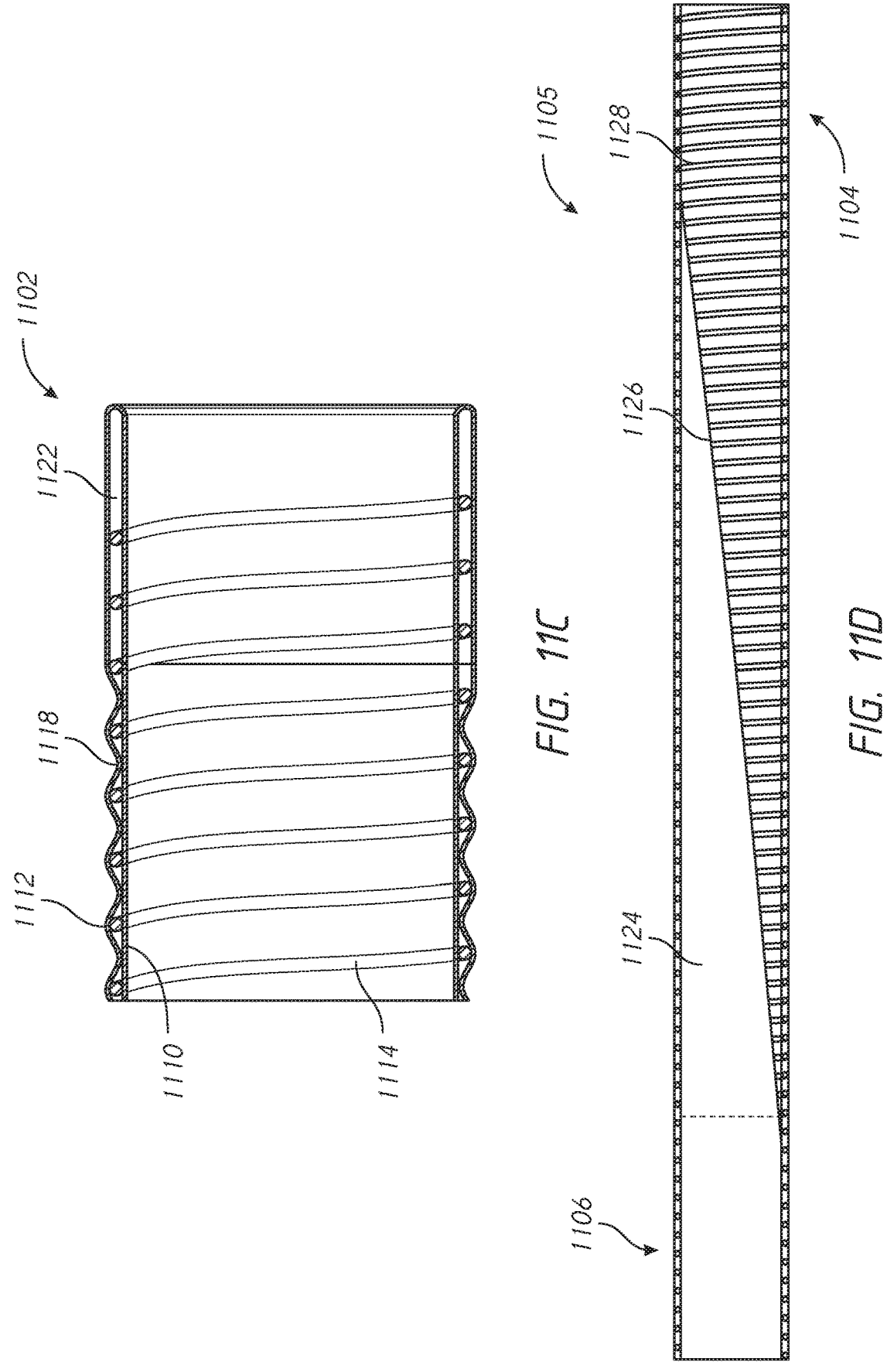

As shown in FIG. 11C, the distal tip 1102 of the catheter 1100 can be cut perpendicular to a longitudinal axis of the catheter 1100. However, in other configurations, the distal tip 1102 can be cut at an oblique angle relative to the longitudinal axis of the catheter 1100. The distal tip 1102 may have a feature (e.g., offset channel or lumen) to force the guidewire to one side of the distal opening to facilitate trackability. In some configurations, the distal tip 1102 can include a soft, flexible tip to create a seal against the emboli surface.

The distal tip 1102 can include a radiopaque marker 1122. As shown in FIG. 11C, the radiopaque marker 1122 can be positioned radially between the inner tubular layer 1110 and the outer tubular layer 1112. The radiopaque marker 1122 can include tungsten, tantalum, platinum alloys, or otherwise. Because of the radiopaque marker 1122, a thickness of the distal tip 1102 may be greater than a region adjacent to the distal tip 1102.

The design of catheter 1100 can be applied to larger diameter catheters having an outer diameter of at least about 5 F and/or less than or equal to about 12 F, between about 8 F and 10 F. It should be noted that this construction could be applied to any catheter diameter, including catheter diameters less than 5 F or greater than 12 F. A wall thickness of the distal portion of any sized catheter (e.g., 5 F, 6 F, 7F, 8 F, 9 F, or otherwise) is less than or equal to about 0.006 inches, or less than or equal to about 0.005 inches.

Catheters 1100 having an outside diameter of at least about 0.05 inches, in some implementations at least about 0.08 inches, or 0.1 inches or 0.2 inches or more can be bent around a radius of curvature for the inside length of less than about 0.1 inches, and in some embodiments less than about 0.08 inches, without kinking.

The distal portion 1104 can have an outer diameter to kink radius ratio of at least about 1.2, or at least about 1.475. Kink radius is the radius at the point when kinking first occurs, so bending the catheter shaft around the kink radius or a smaller radius will cause a kink in the catheter shaft. For example, for a catheter 1100 having an outer diameter of less than or equal to about 9 F, the distal portion 1104 will not kink when bent to form an arcuate portion having a radius (measured from the inner curvature) of no more than about 0.1 inches or no more than about 0.08 inches. As another example, for a catheter 1100 having an outer diameter of less than or equal to about 8.0 F, the distal portion 1104 will not kink when bent to form an arcuate portion having a radius (measured from the inner curvature) of no more than about 0.1 inches or no more than about 0.08 inches.

Although catheter 1100 is described as having a single helical support 1114, other configurations may include additional helical supports axially aligned with the helical support 1114 in a longitudinal dimension.

Figure 12:
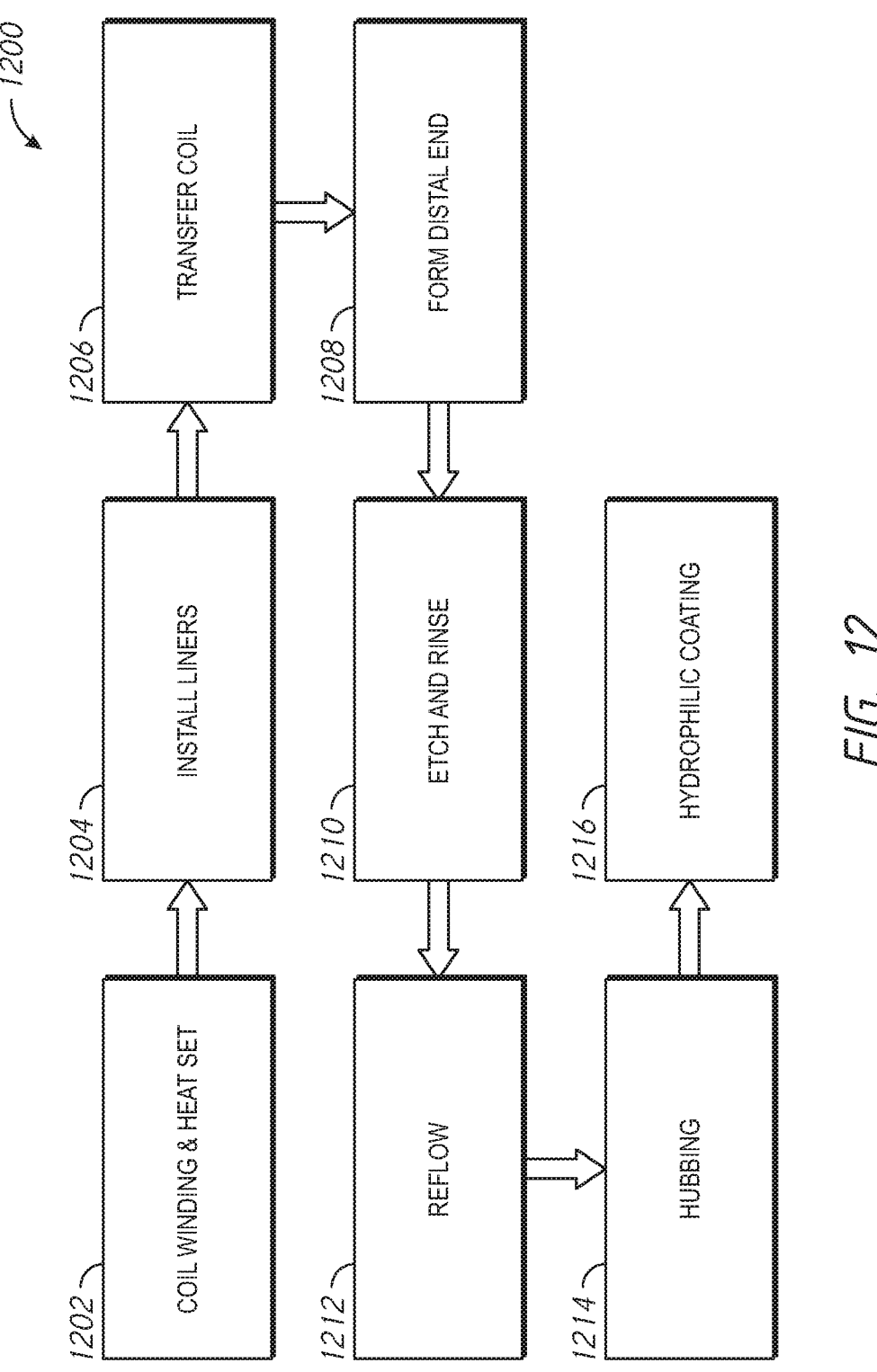
FIG. 12 is a flow chart demonstrating one method of manufacturing the catheter shown in FIG. 11A.

One method of manufacturing the catheter 1100 is described below and outlined in FIG. 12. Although certain materials are described below, other materials can be used as described above. Any step disclosed below can be replaced with or combined with any other step disclosed herein, reordered, or omitted.

In step 1202, the helical support 1114 can by formed by winding a wire onto a mandrel to and heat setting the wire to form a coil.

Separately, in step 1204, a layer of PTFE 1124 can be placed over the catheter mandrel to form at least a portion (e.g., a proximal portion) of the inner tubular layer 1110 of the catheter 1100. The layer of PTFE 1124 can be heat shrunk so the inner tubular layer 1110 remains stationary when the helical support 1114 is transferred to the catheter mandrel. A skived section 1126 is formed at the distal end of the layer of PTFE 1124 (e.g., at least about 1.0 inches long). A layer of ePTFE 1128 is placed over the mandrel so that the layer of ePTFE 1128 extends distally from the layer of PTFE 1124. The layer of ePTFE 1128 will form at least a portion of the inner tubular layer 1110 (e.g., distal portion) and/or the outer tubular layer 1112 of the catheter 1100. The layer of ePTFE 1128 can overlap the skived end 1126 of the PTFE layer 1124 by less than or equal to about 2.0 mm or less than or equal to about 1.0 mm. This skived area facilitates a continuous transition between the two layers of material. The layers of PTFE or ePTFE referred to herein may be tubular segments of material or sheets of material wrapped around the mandrel. In other configurations, the inner tubular layer 1110 may be formed from a single layer, or the inner and outer layers of the distal portion 1104 may be formed from two different segments of material.

In step 1206, the helical support 1114 is transferred to the catheter mandrel. A distal end of the helical support 1114 can be glued to the layer of ePTFE 1126 to hold the helical support 1114 in place during the remaining steps of this process. In instances where the catheter mandrel has an outer diameter that is greater than an inner diameter of the helical support, the helical support 1114 is at least partially stressed.

In step 1208, a radiopaque marker 1122 can be placed in the area of the distal end of the helical support 1114 (step 1208). The radiopaque marker 1122 may overlap the distal end of the helical support 1114. The radiopaque marker 1122 can be shrunk down and melted into that section of the catheter 1100 to form part of the distal tip 1102. The layer of ePTFE 1128 is folded around or inverted over the radiopaque marker 1122 and extended proximally over the helical support 1114 to form the outer tubular layer 1112.

Providing a continuous layer of material from the inside diameter, around the distal tip to the outside diameter reduces the risk that the inner and outer layers will separate and expose the helical support 1114 and/or radiopaque marker 1122. In this configuration, the inner and outer layers 1110, 1112 of at least the distal portion 1104 are constructed from the same segment of material. Another wire is coiled over at least the distal portion 1104 of the outer tubular layer 1112 and in the spaces 1120 between adjacent loops of the helical support 1114. This wire is used to create enough pressure to sinter the inner tubular layer 1110 and the outer tubular layer 1112 in the spaces 1120 between adjacent loops of the helical support 1114. Through this sintering process, a helical channel 1118 is formed between the inner tubular layer 1110 and the outer tubular layer 1112. The helical support 1114 remains unbonded to the helical channel 1118 as discussed above. After the sintering process, the wire is removed. In instances where the inner and outer layers of the distal portion 1104 are formed by different segments of material, the outer layer can be placed over the helical support 1114 and sintered in the spaces 1120 between adjacent loops of the helical support 1114 to form the helical channel 1118.

The proximal portion 1106 of the catheter 110 is etched (step 1210), and then one or more jackets of material are placed over the proximal portion 1106 (step 1212). The polymer jacket can include a material (e.g., polyether block amide) different from the inner and/or outer tubular layers 1110, 1112. The polymer jacket(s) can have a different durometer than the outer tubular layer 1110 to form a stiffer profile. To the extent there are multiple jacket segments, the jacket segments can have different diameters and be arranged from harder durometer to softer durometer in the proximal to distal direction. The one or more jackets are fused together and over the helical support 1114 using standard bonding and reflow methods (step 1212). In step 1216, the proximal hub 1108 is joined to the proximal portion 1106. Optionally, at least the proximal portion 1106 of the catheter 1100 is coated with a hydrophilic coating (1218). The distal portion 1104 of the catheter can remain uncoated.

Corrugated Inner Liner Surface Structure

Figure 13:
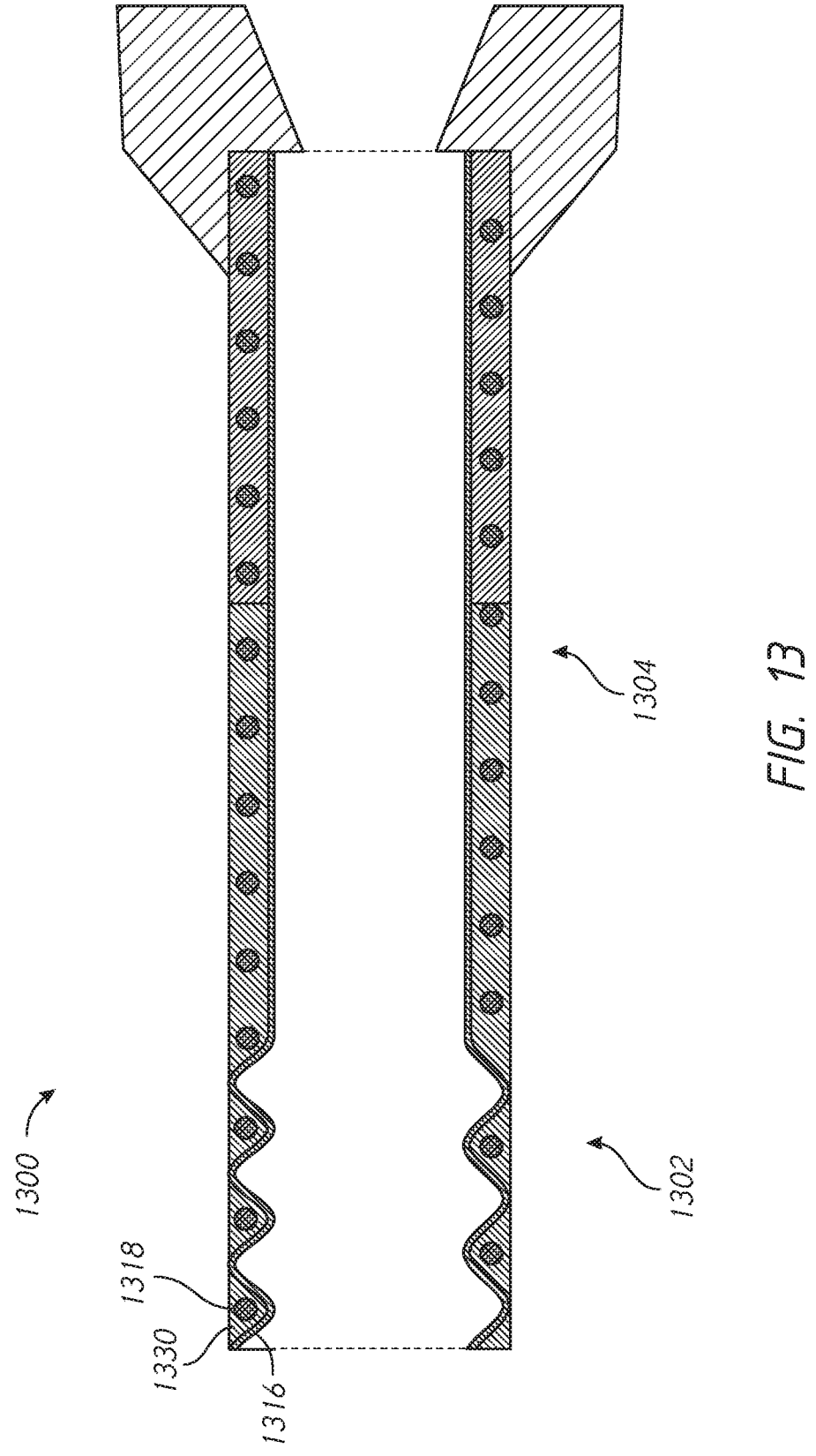
FIG. 13 is a schematic representation of yet another catheter having a single reinforcement structure.

FIG. 13 shows another embodiment of a catheter 1300 where the catheter construction is comprised of a braided/coiled wire reinforcing element 1318 encapsulated in a polymer (e.g., plastic) matrix 1330 in at least a distal portion 1302 of the catheter 1300. The inner liner layer 1316 is not substantially cylindrical in at least a distal portion 1302 of the catheter 1300. The inner layer surface 1316 is constructed in a helical/corrugated shape to allow for a more flexible construct. The flexibility of this structure is achieved by having a section comprised of a coil 1318 encapsulated in the plastic matrix 1330 directly distal/proximal to a thin section where there is only the plastic matrix 1330 with inner liner 1318 without the coil component in spaces between adjacent loops of the coil 1318. This construction allows for enhanced flexibility by allowing a greater deflection at the sections without the coil component compared to the coil-construction region. This pattern of coil-construction and non-coil-construction repeats along a helical pattern along the distal portion 1302 of the device. The proximal portion 1304 can have a similar construction to the proximal portion 504 of catheter 500.

This embodiment can be best fabricated by constructing the "Dual Reinforcement Structure" (e.g., catheters 300, 400) described above and thermally bonding a plastic matrix component 1330 to the external surface of the construction.

Once the plastic matrix 1330 is present, the internal metallic coil component can be removed to have the resultant helical/corrugated shape of the inner layer 1316.

Terminology

The term "catheter" as used herein, is a broad term to be given its ordinary and customary meaning to a person skilled in the art and includes, without limitation, micro catheters, access sheaths, guide catheters, aspiration catheters, balloon catheters, stent delivery catheters, electrophysiology probes, general device tubing, etc.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

The term "generally" as used herein represents a value, amount, or characteristic that predominantly includes or tends toward a particular value, amount, or characteristic. As an example, in certain embodiments, the term "generally uniform" refers to a value, amount, or characteristic that departs from exactly uniform by less than 20%, less than 15%, less than 10%, less than 5%, less than 1%, less than 0.1%, and less than 0.01%.

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about 5.0 cm" includes "5.0 cm."

Some embodiments have been described in connection with schematic drawings. However, it should be understood that the schematic drawings are not drawn to scale. Distances are merely illustrative and do not necessarily bear an exact relationship to actual dimensions and layout of the devices illustrated.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

EXAMPLE EMBODIMENTS

The following example embodiments identify some possible permutations of combinations of features disclosed herein, although other permutations of combinations of features are also possible.

1. A highly flexible, kink resistant catheter with floating tubular support, comprising:
   an elongate tubular body, having a proximal end, a distal end and a central lumen, the tubular body comprising:
   an inner tubular layer surrounding the lumen;
   a helical support, carried concentrically over the inner layer and having adjacent loops spaced axially apart; and
   an outer tubular layer, carried concentrically over the helical support;
   wherein the inner layer and the outer layer are bonded together in the space between adjacent loops of the tubular support to form a helical channel and the helical support is floating unbonded within the helical channel.
2. A highly flexible catheter as in Embodiment 1, wherein at least one of the inner and outer tubular layers comprises ePTFE or electrospun PTFE.
3. A highly flexible catheter as in Embodiment 2, wherein the ePTFE has a wall thickness of no more than about 0.004".
4. A highly flexible catheter as in Embodiment 3, wherein the ePTFE has a wall thickness of no more than about 0.002".
5. A highly flexible catheter as in any one of Embodiment 1 to 4, wherein the helical support comprises Nitinol wire.
6. A highly flexible catheter as in Embodiment 5, wherein the Nitinol wire has a cross section in the radial direction of no more than about 0.006".
7. A highly flexible catheter as in Embodiment 6, wherein the Nitinol wire has a circular cross section having a diameter of about 0.004".
8. A highly flexible catheter as in any one of Embodiments 1 to 7, wherein the inner tubular layer comprises two distinct sections, the two distinct sections comprising a proximal section and a distal section.
9. A highly flexible catheter as in Embodiment 8, wherein the proximal section and the distal section of the inner tubular layer comprise different materials.

10. A highly flexible catheter as in Embodiment 8, wherein the proximal section and the distal section are joined by a skived joint.
11. A highly flexible catheter as in any one of Embodiments 1 to 10, wherein the helical support extends from the distal end to the proximal end of the tubular body.
12. A highly flexible catheter as in any one of Embodiments 1 to 11, wherein a distal portion of the tubular body is more flexible than a proximal portion of the tubular body.
13. A highly flexible catheter as in Embodiment 12, wherein the helical channel only extends through the distal portion of the tubular body.
14. A highly flexible catheter as in any one of Embodiments 1 to 13, wherein the inner tubular layer and the outer tubular layer are formed from a single segment of material in at least a distal portion of the elongate tubular body.
15. A highly flexible catheter as in Embodiment 14, wherein the single segment of material is folded over a distal end of the helical support to form at least a portion of the inner tubular layer and the outer tubular layer.
16. A catheter, comprising:
   an elongate, flexible inner layer positioned concentrically within an elongate, flexible outer layer, the inner and outer layers joined by a helical bond to form a helical channel defined between adjacent bonds; and
   a helical support, floating in the helical channel.
17. A catheter as in Embodiment 16, wherein at least one of the inner and outer layers comprises ePTFE or electrospun PTFE.
18. A catheter as in Embodiment 17, wherein the ePTFE has a wall thickness of no more than about 0.004".
19. A catheter as in Embodiment 18, wherein the ePTFE has a wall thickness of no more than about 0.002".
20. A catheter as in any one of Embodiments 16 to 19, wherein the helical support comprises Nitinol wire.
21. A catheter as in Embodiment 20, wherein the Nitinol wire has a cross section in the radial direction of no more than about 0.006".
22. A catheter as in Embodiment 20, wherein the Nitinol wire has a circular cross section having a diameter of about 0.004".
23. A catheter as in any one of Embodiments 16 to 22, wherein the inner layer comprises two distinct sections, the two distinct sections comprising a proximal section and a distal section.
24. A catheter as in Embodiment 23, wherein the proximal section and the distal section of the inner tubular layer comprise different materials.
25. A catheter as in Embodiment 23, wherein the proximal section and the distal section are joined by a skived joint.
26. A catheter as in any one of Embodiments 16 to 25, wherein the helical support extends from a distal end to a proximal end of the catheter.
27. A catheter as in any one of Embodiments 16 to 26, wherein a distal portion of the catheter is more flexible than a proximal portion of the catheter.
28. A catheter as in Embodiment 27, wherein the helical channel only extends through the distal portion of the catheter.

29. A catheter as in any one of Embodiments 16 to 28, wherein the inner layer and the outer layer are formed from a single segment of material in at least a distal portion of the catheter.

30. A catheter as in Embodiment 29, wherein the single segment of material is folded over a distal end of the helical support to form at least a portion of the inner tubular layer and the outer tubular layer.

31. An enhanced flexibility catheter shaft, comprising:
an elongate flexible body, having a proximal end, a distal end, and at least one lumen extending therethrough;
a distal, flexible section on the body, comprising a tubular membrane having a first helical support on a radially exterior surface of the membrane and a second helical support on a radially interior surface of the membrane.

32. An enhanced flexibility catheter shaft as in Embodiment 31, wherein at least one of the first and second helical supports comprises a nitinol wire.

33. An enhanced flexibility catheter shaft as in Embodiments 31 or 32, wherein an inside diameter of the first helical support is less than an inside diameter of the second helical support.

34. An enhanced flexibility catheter shaft of any one of Embodiments 31 to 33, wherein a pitch of the first helical support is within the range of from about 0.010 inches to about 0.030 inches.

35. An enhanced flexibility catheter shaft as in Embodiment 34, wherein a pitch of the first helical support is within the range of from about 0.015 inches to about 0.025 inches.

36. An enhanced flexibility catheter shaft as in any one of Embodiments 31 to 35, wherein at least the first helical support comprises a wire having a diameter within the range of from about 0.003 inches to about 0.007 inches.

37. An enhanced flexibility catheter shaft as in any one of Embodiments 31 to 36, wherein at least one of the first and second helical supports is floating with respect to the tubular membrane.

38. An enhanced flexibility catheter shaft as in Embodiment 37, wherein both of the first and second helical supports are floating with respect to the tubular membrane.

39. An enhanced flexibility catheter shaft as in any one of Embodiments 31 to 38, wherein the distal, flexible section has an axial length of at least about 1.0 cm.

40. An enhanced flexibility catheter shaft as in Embodiment 39, wherein the distal, flexible section has an axial length of at least about 15 cm.

41. An enhanced flexibility catheter shaft as in Embodiment 33, wherein an inside diameter of the second helical support is at least about 2% greater than the inside diameter of the first helical support.

42. An enhanced flexibility catheter shaft as in Embodiment 41, wherein an inside diameter of the second helical support is about 0.105 inches and the inside diameter of the first helical support is about 0.100 inches.

43. An enhanced flexibility catheter shaft as in any one of Embodiments 31 to 42, wherein the membrane comprises PTFE.

44. An enhanced flexibility catheter shaft as in any one of Embodiments 31 to 43, wherein the membrane comprises ePTFE.

45. An enhanced flexibility catheter shaft as in any one of Embodiments 31 to 44, further comprising a proximal section, having less flexibility than the distal section.

46. An enhanced flexibility catheter shaft as in Embodiment 45, further comprising an intermediate section, having less flexibility than the distal section and greater flexibility than the proximal section.

47. An enhanced flexibility catheter shaft as in Embodiment 46, wherein the tubular membrane extends proximally from the distal section at least at least part way across the intermediate section.

48. An enhanced flexibility catheter shaft as in Embodiment 47, wherein the tubular membrane extends proximally from the distal section at least as far as the proximal section.

49. An enhanced flexibility catheter shaft as in any one of Embodiments 31 to 48, wherein the tubular membrane comprises a helical pleat.

50. An enhanced flexibility catheter shaft as in any one of Embodiments 31 to 49, wherein the distal, flexible section has an outer diameter of at least about 4 French and a % bending load of no more than about 30.

51. An enhanced flexibility catheter shaft as in any one of Embodiments 31 to 49, wherein the distal, flexible section has an outer diameter of at least about 4 French and a % bending load of no more than about 20.

52. An enhanced flexibility catheter shaft as in any one of Embodiments 31 to 49, wherein the distal, flexible section has an outer an outer diameter of at least about 6 French and a % bending load of no more than about 50.

53. An enhanced flexibility catheter shaft as in any one of Embodiments 31 to 49, wherein the distal, flexible section has an outer diameter of at least about 6 French and a % bending load of no more than about 40.

54. An enhanced flexibility catheter shaft as in any one of Embodiments 31 to 49, wherein the distal, flexible section has an outer diameter of at least about 6 French and a % bending load of no more than about 30.

55. An enhanced flexibility catheter shaft as in any one of Embodiments 31 to 49, wherein the distal, flexible section has an outer diameter of at least about 8 French and a % bending load of no more than about 60.

56. An enhanced flexibility catheter shaft as in any one of Embodiments 31 to 49, wherein the distal, flexible section has an outer diameter of at least about 8 French and a % bending load of no more than about 40.

57. An enhanced flexibility catheter shaft as in any one of Embodiments 31 to 49, wherein the distal, flexible section has an outer diameter of at least about 10 French and a % bending load of no more than about 80.

58. An enhanced flexibility catheter shaft as in any one of Embodiments 31 to 49, wherein the distal, flexible section has an outer diameter of at least about 10 French and a % bending load of no more than about 60.

59. An enhanced flexibility catheter shaft as in any one of Embodiments 31 to 49, wherein the distal, flexible section has an outer diameter of at least about 10 French and a % bending load of no more than about 40.

60. An enhanced flexibility catheter shaft, comprising:
an elongate flexible tubular body, having a proximal end, a distal end, and at least one lumen extending therethrough;
a distal, flexible section on the body, comprising a tubular membrane having an outside surface with a plurality of radially outwardly extending annular ribs spaced apart by radially inwardly extending recesses, and an inside surface with a plurality of radially inwardly facing annular concavities corresponding to the radially outwardly extending annular ribs, and an annular support carried within at least one of the radially inwardly extending recesses and the radially inwardly facing annular concavities.

61. An enhanced flexibility catheter shaft as in Embodiment 60, wherein the plurality of radially outwardly extending annular ribs comprise revolutions of a continuous helical rib.

62. An enhanced flexibility catheter shaft as in Embodiment 60, wherein the plurality of radially outwardly extending annular ribs comprises discrete rings spaced apart axially along the distal section.

63. An enhanced flexibility catheter shaft as in any one of Embodiments 60 to 62, comprising a first helical support extending within the radially inwardly extending recesses.

64. An enhanced flexibility catheter shaft as in Embodiment 63, comprising a second helical support extending within the radially inwardly facing annular concavities.

65. An enhanced flexibility catheter shaft as in any one of Embodiments 60 to 64, wherein the annular support is unattached to the adjacent tubular membrane.

66. An enhanced flexibility catheter shaft as in Embodiment 64, wherein the membrane extends in between the first helical support and the second helical support without being bonded to at least one of the first helical support and the second helical support along a length of the distal section.

67. An enhanced flexibility catheter shaft as in Embodiment 64, wherein the membrane extends in between the first helical support and the second helical support without being bonded to either of the first helical support and the second helical support along a length of the distal section.

68. An enhanced flexibility catheter shaft, comprising:

an elongate flexible tubular body, having a proximal end, a distal end, and at least one lumen extending therethrough;

a distal, flexible section on the body, comprising a corrugated tubular membrane;

a first spiral support carried on the outside surface of the tubular membrane; and a second spiral support carried on the inside surface of the tubular membrane;

wherein at least one of the first and second spiral supports is floating with respect to the adjacent membrane.

69. An enhanced flexibility catheter shaft as in Embodiment 68, wherein both of the first and second spiral supports are floating with respect to the adjacent membrane.

70. An enhanced flexibility catheter shaft, comprising:

an elongate flexible tubular body, having a proximal end, a distal end, and at least one lumen extending therethrough; and a distal, flexible section on the body, comprising a corrugated tubular membrane;

wherein the tubular body has an outer diameter of at least about 6 French and a % bending load of no more than about 40.

What is claimed is:

1. A catheter comprising:

a body having a proximal portion, a distal portion, and a central lumen, in which the distal portion is more flexible than the proximal portion, the body comprising:

an inner tubular membrane defining the central lumen, the inner tubular membrane extending proximally and providing an inner-most lining of the proximal portion, and one or more reinforcement structures, carried concentrically over the inner tubular membrane, the one or more reinforcement structures providing a proximal support extending proximally along a length of the catheter and being encapsulated in one or more sections of polymer tubing, wherein the inner tubular membrane in the distal portion forms a continuous helical groove extending around an entire circumference of the catheter forming corrugations that are spaced apart substantially perpendicularly to a longitudinal axis that extends from a proximal end to a distal end of the catheter, wherein the inner tubular membrane in the proximal portion forms a substantially cylindrical inner liner, wherein the one or more reinforcement structures, collectively, are carried concentrically over the inner tubular membrane in the distal portion and the proximal portion along an entire length of the catheter, wherein the catheter has an outer-most surface that is smooth in the distal portion and an inner-most surface formed by the corrugations, the corrugations extend inwardly towards a central longitudinal axis of the central lumen, and wherein the one or more reinforcement structures includes a helical support or a braided structure.

2. The catheter of claim 1, wherein the one or more reinforcement structures include a first reinforcement structure and a second reinforcement structure.

3. The catheter of claim 2, wherein a first portion of the first reinforcement structure and a second portion of the second reinforcement structure overlap along the longitudinal axis that extends from the proximal end to the distal end of the catheter.

4. The catheter of claim 1, wherein the outer-most surface of the catheter is smooth proximally of the distal portion.

5. The catheter of claim 1, wherein the inner tubular membrane comprises ePTFE material, and a wall thickness of the ePTFE is no more than about 0.10 mm.

6. The catheter of claim 1, wherein the one or more reinforcement structures includes the helical support, and wherein a depth of the continuous helical groove is at least about 1 times a diameter of wire forming the helical support.

7. The catheter of claim 1, wherein the one or more reinforcement structures includes the helical support, and wherein the helical support is positioned in the continuous helical groove in the distal portion such that a helical rib extends through interstitial spaces of the helical support.

8. The catheter of claim 7, wherein the one or more reinforcement structures includes the helical support, and wherein a depth of the continuous helical groove of the inner tubular membrane is at least about 1.00 times a diameter of wire forming the helical support.

9. The catheter of claim 1, wherein the inner tubular membrane comprises two distinct sections, the two distinct sections comprising a proximal section and a distal section.

10. The catheter of claim 1, wherein the one or more reinforcement structures includes the helical support, and wherein the helical support is encapsulated entirely by the one or more sections of polymer tubing.

11. The catheter of claim 1, wherein the one or more reinforcement structures includes the helical support, and wherein the helical support terminates in the distal portion.

12. The catheter of claim 1, wherein the one or more reinforcement structures includes the helical support, and wherein the helical support extends proximally of the distal portion to provide support to the proximal portion to prevent kinking and the helical support is encapsulated in the proximal portion in the one or more sections of polymer tubing.

13. The catheter of claim 1, wherein the one or more reinforcement structures includes the helical support, and wherein the helical support is comprised of Nitinol wire and has a cross section in a radial direction of no more than about 0.15 mm (0.006 inches).

14. The catheter of claim 1, wherein the one or more reinforcement structures includes the helical support, and wherein the helical support comprises a same material along an entire length of the helical support.

15. The catheter of claim 1, wherein the inner tubular membrane has a thickness of no more than about 0.10 mm (0.004 inches).

16. A catheter comprising:
a body having a proximal portion, a distal portion, and a central lumen, in which the distal portion is more flexible than the proximal portion, the body comprising:
an inner tubular membrane surrounding the central lumen, the inner tubular membrane extending proximally and providing an inner-most lining of the proximal portion, and
one or more reinforcement structures, carried concentrically over the inner tubular membrane, the one or more reinforcement structures providing a proximal support extending proximally along a length of the catheter and being encapsulated in one or more sections of polymer tubing,
wherein the inner tubular membrane in the distal portion forms a continuous helical groove portion extending around an entire circumference of the catheter, the distal portion of the body including an outer-most surface that is smooth and an inner-most surface formed by inwardly facing helical corrugations,
wherein the one or more reinforcement structures are provided within the helical corrugations of the distal portion, wherein the inner tubular membrane in the proximal portion forms a non-corrugated inner liner,
wherein the one or more reinforcement structures, collectively, are carried concentrically over the inner tubular membrane in the distal portion and the proximal portion along an entire length of the catheter,
wherein the one or more reinforcement structures includes a helical support or a braided structure, and
wherein the helical corrugations are spaced apart substantially perpendicularly to a longitudinal axis that extends from a proximal end to a distal end of the catheter.

17. The catheter of claim 16, wherein the one or more sections of polymer tubing cover an entire outer surface of the inner tubular membrane, and form the outer-most surface of the catheter.

18. The catheter of claim 16, wherein the one or more reinforcement structures includes the helical support, and wherein the helical support is encapsulated entirely by the one or more sections of polymer tubing.

19. A catheter comprising:
an elongate tubular body having a proximal portion, a distal portion, and a central lumen, in which the distal portion is more flexible than the proximal portion, the elongate tubular body comprising:
an inner tubular membrane defining the central lumen, the inner tubular membrane extending proximally and providing an inner-most lining of the proximal portion, and
one or more reinforcement structures, collectively, carried concentrically over the inner tubular membrane in the distal portion and the proximal portion along an entire length of the catheter,
wherein the inner tubular membrane in the distal portion forms a continuous helical groove extending around an entire circumference of the catheter forming corrugations that are spaced apart substantially perpendicularly to a longitudinal axis that extends from a proximal end to a distal end of the catheter, the distal portion including an outer-most surface that is smooth,
wherein the corrugations form the inner-most surface of the distal portion and extend towards a longitudinal axis of the central lumen, and
wherein the one or more reinforcement structures includes a helical support or a braided structure.

20. The catheter of claim 19, wherein the inner tubular membrane comprises two distinct sections, the two distinct sections comprising a proximal section and a distal section.

* * * * *